United States Patent
Kanda et al.

(10) Patent No.: US 9,916,666 B2
(45) Date of Patent: Mar. 13, 2018

(54) IMAGE PROCESSING APPARATUS FOR IDENTIFYING WHETHER OR NOT MICROSTRUCTURE IN SET EXAMINATION REGION IS ABNORMAL, IMAGE PROCESSING METHOD, AND COMPUTER-READABLE RECORDING DEVICE

(71) Applicant: OLYMPUS CORPORATION, Tokyo (JP)

(72) Inventors: Yamato Kanda, Hino (JP); Makoto Kitamura, Hachioji (JP); Takashi Kono, Tachikawa (JP); Masashi Hirota, Hachioji (JP); Toshiya Kamiyama, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 92 days.

(21) Appl. No.: 14/564,453

(22) Filed: Dec. 9, 2014

(65) Prior Publication Data

US 2015/0092993 A1 Apr. 2, 2015

Related U.S. Application Data

(63) Continuation of application No. PCT/JP2013/064332, filed on May 23, 2013.

(30) Foreign Application Priority Data

Jun. 12, 2012 (JP) .................................. 2012-133187

(51) Int. Cl.
*G06K 9/00* (2006.01)
*H04N 13/02* (2006.01)
(Continued)

(52) U.S. Cl.
CPC ............ *G06T 7/40* (2013.01); *A61B 1/00009* (2013.01); *G06T 7/0012* (2013.01); *A61B 1/0676* (2013.01);
(Continued)

(58) Field of Classification Search
None
See application file for complete search history.

(56) References Cited

U.S. PATENT DOCUMENTS 8,107,698 B2  1/2012  Kitamura
2005/0100208 A1*  5/2005  Suzuki .................... G06T 5/007
382/157

(Continued)

FOREIGN PATENT DOCUMENTS

CN  103198467 A  7/2013
EP  2 405 397 A1  1/2012
(Continued)

OTHER PUBLICATIONS

Extended Supplementary European Search Report dated Feb. 19, 2016 from related European Application No. 13 80 3772.6.
(Continued)

*Primary Examiner* — Randolph I Chu
(74) *Attorney, Agent, or Firm* — Scully, Scott, Murphy & Presser, P.C.

(57) ABSTRACT

An image processing apparatus includes: an imaging distance estimating unit configured to estimate an imaging distance to a subject shown in an image; an examination region setting unit configured to set an examination region in the image such that an index indicating a spread of a distribution of imaging distances to the subject shown in the examination region is within a given range; and an abnormal structure identifying unit configured to identify whether or not a microstructure of the subject shown in the examination (Continued)

region is abnormal, by using texture feature data that enables identification of an abnormality in the microstructure of the subject shown in the examination region, the texture feature data being specified according the examination region.

18 Claims, 26 Drawing Sheets

(51) Int. Cl.
    *A62B 1/04*     (2006.01)
    *G06T 7/40*     (2017.01)
    *A61B 1/00*     (2006.01)
    *G06T 7/00*     (2017.01)
    *A61B 1/06*     (2006.01)

(52) U.S. Cl.
    CPC ............... *G06T 2207/10024* (2013.01); *G06T 2207/10068* (2013.01); *G06T 2207/30028* (2013.01); *G06T 2207/30101* (2013.01)

(56) References Cited

U.S. PATENT DOCUMENTS

| | | | | |
|---|---|---|---|---|
| 2007/0036414 | A1* | 2/2007 | Georgescu | G06T 7/0083 382/128 |
| 2008/0279431 | A1* | 11/2008 | Kitamura | A61B 1/00009 382/128 |
| 2009/0322863 | A1* | 12/2009 | Takahashi | G01C 3/00 348/65 |
| 2010/0119110 | A1 | 5/2010 | Kanda | |
| 2012/0051612 | A1* | 3/2012 | Kitamura | G06T 7/0012 382/128 |
| 2012/0051654 | A1* | 3/2012 | Kitamura | G06T 7/0089 382/199 |
| 2012/0076372 | A1* | 3/2012 | Nishimura | A61B 1/05 382/128 |
| 2013/0027532 | A1* | 1/2013 | Hirota | G06T 7/0012 348/65 |
| 2013/0028485 | A1 | 1/2013 | Kitamura et al. | |
| 2013/0051642 | A1* | 2/2013 | Kanda | G06T 7/0012 382/128 |
| 2014/0257114 | A1* | 9/2014 | Hirota | A61B 1/041 600/476 |
| 2014/0270377 | A1* | 9/2014 | Kanda | A61B 1/00009 382/103 |
| 2015/0254826 | A1* | 9/2015 | Kanda | G06T 7/0012 382/128 |
| 2015/0356369 | A1* | 12/2015 | Kitamura | G06T 7/0014 382/128 |

FOREIGN PATENT DOCUMENTS

| | | |
|---|---|---|
| EP | 2 551 821 A1 | 1/2013 |
| JP | 03-105483 A | 5/1991 |
| JP | H03-105483 A | 5/1991 |
| JP | 2918162 A | 7/1999 |
| JP | 2002-165757 A | 6/2002 |
| JP | 2005-192880 A | 7/2005 |
| JP | 2006-141734 A | 6/2006 |
| JP | 2008-278964 A | 11/2008 |
| JP | 2010-113616 A | 5/2010 |
| WO | WO 2011/129176 A | 10/2011 |
| WO | WO 2011/129176 A1 | 10/2011 |

OTHER PUBLICATIONS

Japanese Office Action dated Mar. 7, 2017 in Japanese Patent Application No. 2012-133187.
International Search Report dated Aug. 27, 2013 issued in PCT/JP2013/064332.
English Abstract of JP 02-124131, dated May 11, 1990.

\* cited by examiner

IMAGE PROCESSING APPARATUS FOR IDENTIFYING WHETHER OR NOT MICROSTRUCTURE IN SET EXAMINATION REGION IS ABNORMAL, IMAGE PROCESSING METHOD, AND COMPUTER-READABLE RECORDING DEVICE

CROSS-REFERENCE TO RELATED APPLICATIONS

This application is a continuation of PCT international application Ser. No. PCT/JP2013/064332 filed on May 23, 2013 which designates the United States, incorporated herein by reference, and which claims the benefit of priority from Japanese Patent Application No. 2012-133187, filed on Jun. 12, 2012, incorporated herein by reference.

BACKGROUND

1. Technical Field

The disclosure relates to an image processing apparatus, an image processing method, and a computer-readable recording device, for identifying an abnormal part region from an image acquired by imaging inside of a lumen of a living body.

2. Related Art

As image processing on an image acquired by imaging inside of a lumen of a living body by a medical observation apparatus, such as an endoscope or a capsule endoscope (hereinafter, referred to as "endoscope image" or "intraluminal image", or simply as "image"), a technique is disclosed in Japanese Patent Application Laid-open No. 2005-192880, for example, which is for detecting, from an image, an abnormal part based on a microstructure of a mucosal surface or a blood stream form. In this technique, after extracting, from an endoscope image, an image composed of a green (G) component including a lot of information related to a microstructure of a mucosa or to a blood stream image, feature data numerically expressing a pixel value pattern of the mucosal surface are calculated, and whether or not a subject shown in the image is normal or abnormal is identified by using the feature data and a linear discriminant function generated beforehand. As the feature data, for example, shape feature data (area, groove width, peripheral length, circularity, branch point, edge point, branching rate, or the like; for example, see Japanese Patent No. 2918162) of a region extracted by binarizing an image of a particular spatial frequency component, or feature data based on spatial frequency analysis using Gabor filter or the like (for example, see Japanese Patent Application Laid-open No. 2002-165757) are used. Further, the linear discriminant function is generated beforehand with teacher data, which are feature data calculated from images of normal and abnormal findings.

SUMMARY

In some embodiments, an image processing apparatus includes: an imaging distance estimating unit configured to estimate an imaging distance to a subject shown in an image; an examination region setting unit configured to set an examination region in the image such that an index indicating a spread of a distribution of imaging distances to the subject shown in the examination region is within a given range; and an abnormal structure identifying unit configured to identify whether or not a microstructure of the subject shown in the examination region is abnormal, by using texture feature data that enables identification of an abnormality in the microstructure of the subject shown in the examination region, the texture feature data being specified according the examination region.

In some embodiments, an image processing method includes: an imaging distance estimating step of estimating an imaging distance to a subject shown in an image; an examination region setting step of setting an examination region in the image such that an index indicating a spread of a distribution of imaging distances to the subject shown in the examination region is within a given range; and an abnormal structure identifying step of identifying whether or not a microstructure of the subject shown in the examination region is abnormal, by using texture feature data that enables identification of an abnormality in the microstructure of the subject shown in the examination region, the texture feature data being specified according the examination region.

In some embodiments, a computer-readable recording device with an executable program stored thereon is provided. The program instructs a processor to perform: an imaging distance estimating step of estimating an imaging distance to a subject shown in an image; an examination region setting step of setting an examination region in the image such that an index indicating a spread of a distribution of imaging distances to the subject shown in the examination region is within a given range; and an abnormal structure identifying step of identifying whether or not a microstructure of the subject shown in the examination region is abnormal, by using texture feature data that enables identification of an abnormality in the microstructure of the subject shown in the examination region, the texture feature data being specified according the examination region.

The above and other features, advantages and technical and industrial significance of this invention will be better understood by reading the following detailed description of presently preferred embodiments of the invention, when considered in connection with the accompanying drawings.

DETAILED DESCRIPTION

Hereinafter, an image processing apparatus, an image processing method, and an image processing program according to embodiments of the present invention will be described with reference to the drawings. The present invention is not to be limited by these embodiments. The same reference signs are used to designate the same elements throughout the drawings.

First Embodiment

Figure 1:
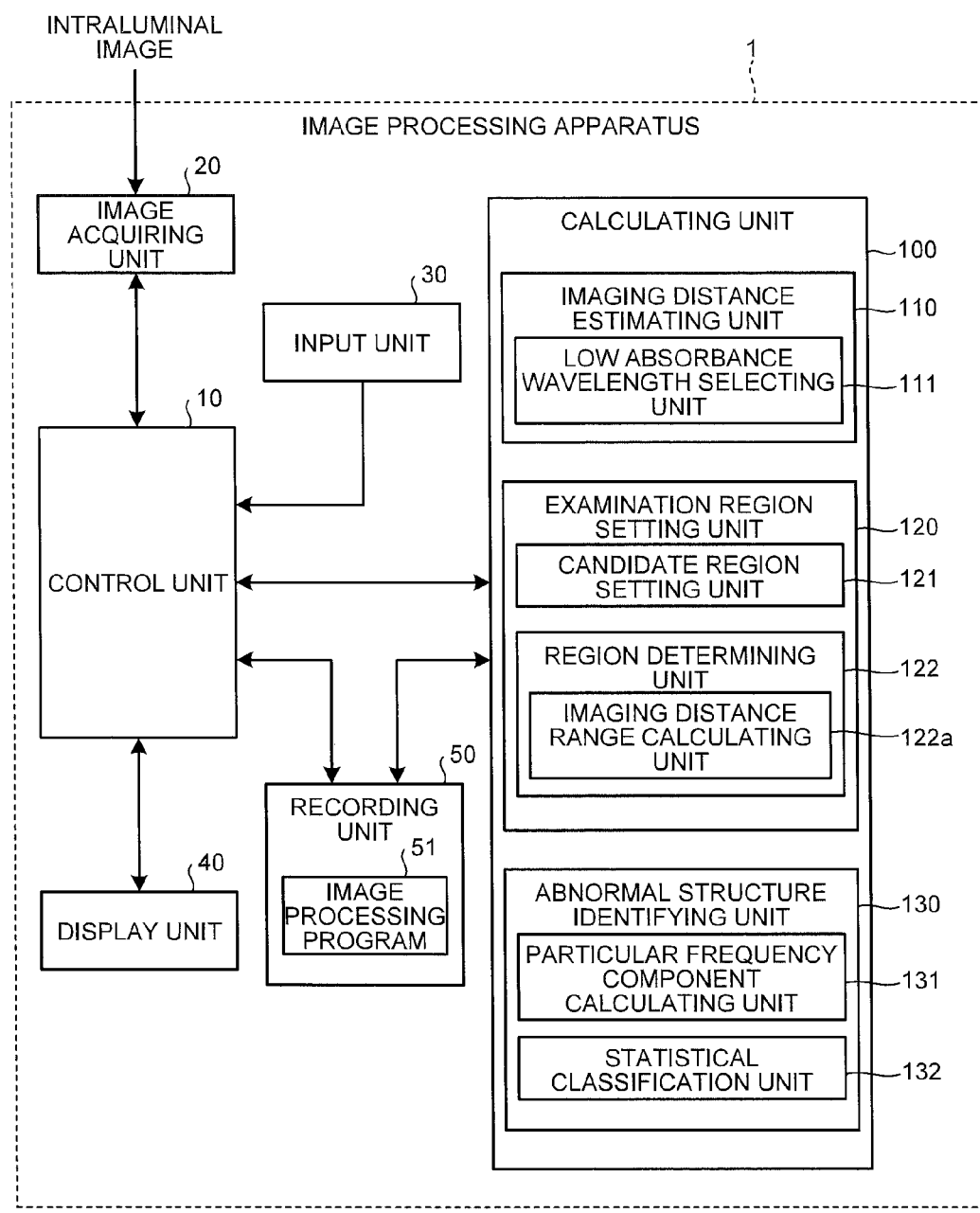
FIG. 1 is a block diagram illustrating a configuration of an image processing apparatus according to a first embodiment of the present invention.

FIG. 1 is a block diagram illustrating a configuration of an image processing apparatus according to a first embodiment of the present invention. An image processing apparatus 1 according to the first embodiment, as an example, is an apparatus that performs image processing for identifying an abnormality in a microstructure of a mucosal surface with respect to an intraluminal image (hereinafter, simply referred to as "image") acquired by imaging inside a lumen of a living body by using an endoscope or a capsule endoscope (hereinafter, these will both be simply referred to as "endoscope"). The intraluminal image is normally a color image having given (for example, 256-gradation) pixel levels (pixel values) for red (R), green (G), and blue (B) wavelength components (color components) at each pixel position.

As illustrated in FIG. 1, the image processing apparatus 1 includes: a control unit 10 that controls operations of the overall image processing apparatus 1; an image acquiring unit 20 that acquires image data corresponding to the image captured by the endoscope; an input unit 30 that receives an input signal input from outside; a display unit 40 that performs various displays; a recording unit 50 that stores therein the image data acquired by the image acquiring unit 20 and various programs; and a calculating unit 100 that executes specified image processing on the image data.

The control unit 10 is realized by hardware, such as a CPU, and by reading the various programs recorded in the recording unit 50, performs transfer or the like of instructions and data to respective units forming the image processing apparatus 1 according to the image data input from the image acquiring unit 20 and an operation signal and the like input from the input unit 30 and comprehensively controls the operations of the overall image processing apparatus 1.

The image acquiring unit 20 is configured as appropriate according to a mode of a system including the endoscope. For example, if a portable recording medium is used in transfer of image data to and from the capsule endoscope, the image acquiring unit 20 is configured of a reader device, to which this recording medium is detachably attached, and which reads the recorded image data of the image. Further, if a server to store therein the image data of the image captured by the endoscope is to be arranged, the image acquiring unit 20 is configured of a communication device or the like connected to the server and performs data communication with the server to acquire the image data. Or, the image acquiring unit 20 may be configured of an interface device or the like that inputs an image signal from the endoscope via a cable.

The input unit 30 is realized by an input device, such as a key board and a mouse, a touch panel, or various switches, and outputs the received input signal to the control unit 10.

The display unit 40 is realized by a display device, such as an LCD or an EL display, and under the control by the control unit 10, displays various screens including the intraluminal image.

The recording unit 50 is realized by: various IC memories, such as a ROM and a RAM like rewritable flash memories; a built-in hard disk or a hard disk connected via a data communication terminal; an information recording device such as a CD-ROM and a reading device thereof; or the like. The recording unit 50 stores therein the image data acquired by the image acquiring unit 20, as well as a program for causing the image processing apparatus 1 to operate and causing the image processing apparatus 1 to execute various functions, data used during the execution of this program, and the like. Specifically, the recording unit 50 stores therein an image processing program 51 for identifying an abnormality in a microstructure of a mucosal surface shown in an image, various information used during execution of this program, and the like.

The calculating unit 100 is realized by hardware such as a CPU, and by reading the image processing program 51, performs the image processing on the intraluminal image and executes various calculating processes for identifying an abnormality in a microstructure of a mucosal surface.

Next, a detailed configuration of the calculating unit 100 will be described.

As illustrated in FIG. 1, the calculating unit 100 includes: an imaging distance estimating unit 110 that estimates an imaging distance to a subject shown in an image; an examination region setting unit 120 that sets an examination region in the image, such that an index indicating a spread of a distribution of imaging distance of the subject shown in the examination region is within a given range; and an abnormal structure identifying unit 130 that identifies, by using texture feature data enabling identification of an abnormality in a microstructure of the subject shown in the examination region, whether or not the microstructure of the subject shown in the examination region is abnormal, the texture feature data being specified according to the examination region.

The texture in the image processing herein is a repeated brightness pattern (reference: "Digital Image Processing" by CG-ARTS Society, page 192 ("Texture of Region")). In this first embodiment, a particular spatial frequency component is used as the texture feature data numerically expressing a feature of the texture.

Of the configuration of the calculating unit 100, the imaging distance estimating unit 110 includes a low absorbance wavelength selecting unit 111 that selects, from pixel values (respective values of R-component, G-component, and B-component) of each pixel in the image, a value of the R-component (hereinafter, referred to as "R-component value") corresponding to a low absorbance wavelength component, which is a wavelength component having the lowest degree of absorption or scattering in the living body, and the imaging distance estimating unit 110 estimates the imaging distance to the subject shown in the image, based on the R-component value.

The examination region setting unit 120 includes a candidate region setting unit 121 that sets an examination candidate region in the image and a region determining unit 122 that determines the examination region based on imaging distance information of the subject shown in the set examination candidate region. Of these, the region determining unit 122 includes an imaging distance range calculating unit 122a that calculates a distribution range of imaging distance to the subject shown in the examination candidate region, and the region determining unit 122 determines the examination candidate region with the distribution range equal to or less than a given threshold value to be the examination region.

The abnormal structure identifying unit 130 includes a particular frequency component calculating unit 131 that calculates a particular spatial frequency component in the examination region and a statistical classification unit 132 that performs statistical classification based on the particular spatial frequency component. The particular spatial frequency component will be described later.

Figure 2:
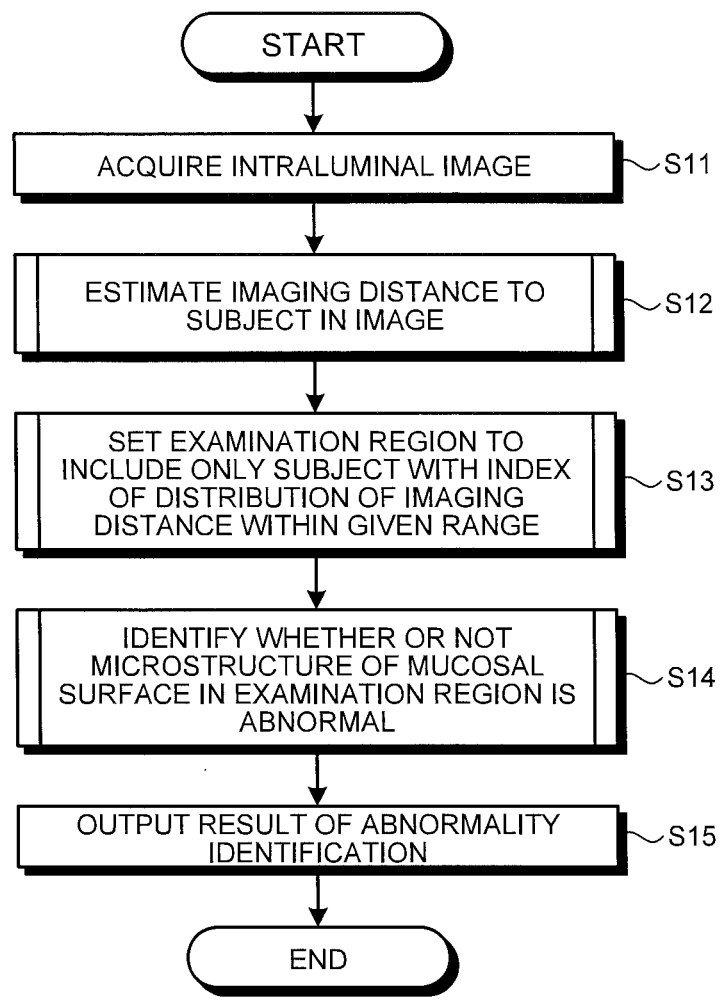
FIG. 2 is a flow chart illustrating operations of the image processing apparatus illustrated in FIG. 1.

Next, operations of the image processing apparatus 1 will be described. FIG. 2 is a flow chart illustrating operations of the image processing apparatus 1. In this first embodiment, a mucosa is assumed to be shown in most of the regions of the intraluminal image and hereinafter, a process with respect to a mucosa area will be described.

First, at Step S11, the calculating unit 100 acquires, by reading the image data recorded in the recording unit 50, an intraluminal image to be processed.

Figure 3A:
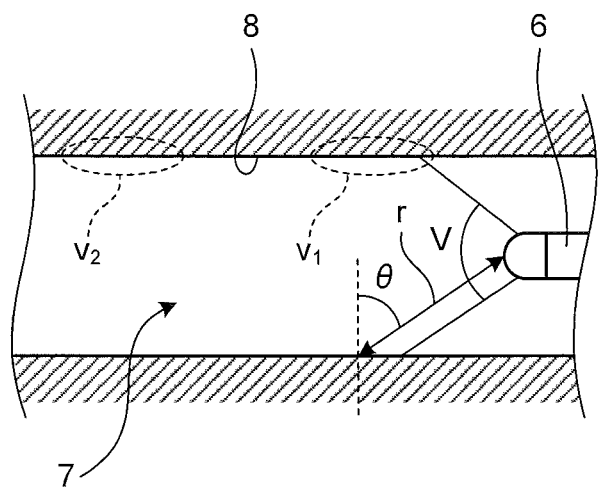
FIG. 3A is a schematic diagram illustrating how inside of a lumen is imaged by an endoscope.
Figure 3B:
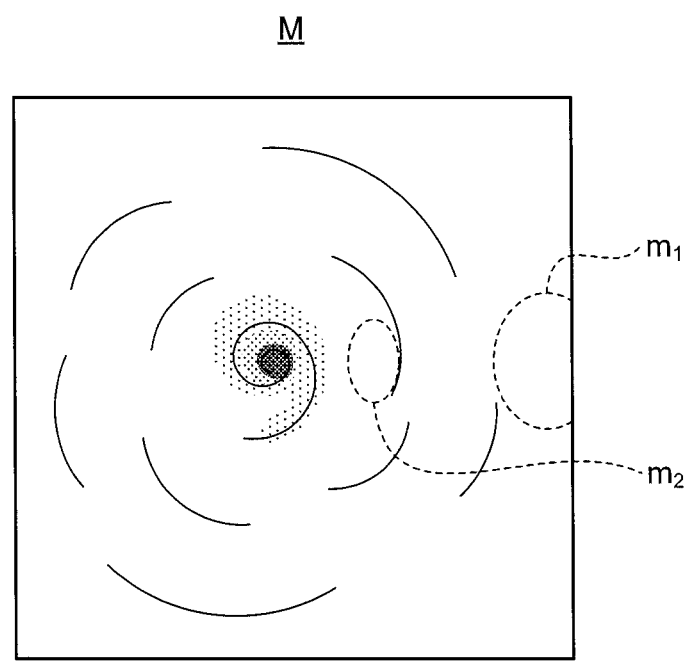
FIG. 3B is a schematic diagram illustrating an intraluminal image captured by the endoscope.

FIG. 3A is a schematic diagram illustrating how the inside of a lumen is imaged by an endoscope. Further, FIG. 3B is a schematic diagram illustrating the intraluminal image captured by the endoscope. An endoscope 6 performs imaging with a visual field "V" directed in a longitudinal direction of a lumen 7. Thus, in an image "M" having a mucosal surface 8, which is a subject shown therein, an image region $m_1$ having a near view $v_1$ taken therein and an image region $m_2$ having a distant view $v_2$ shown therein coexist. Therefore, due to a difference in imaging distance "r", a difference in image quality is caused between the image region $m_1$ and the image region $m_2$. Hereinafter, as an example, the image "M" will be described as a target to be processed.

Figure 4:
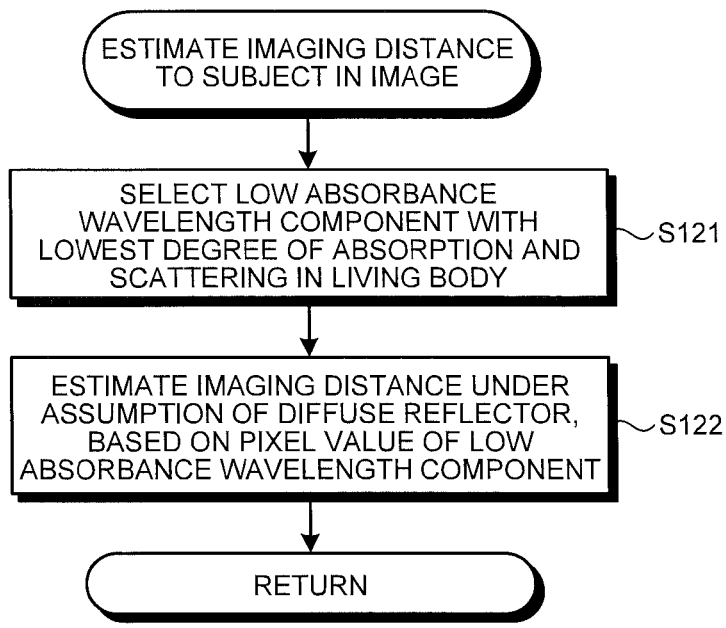
FIG. 4 is a flow chart illustrating in detail a process executed by an imaging distance estimating unit illustrated in FIG. 1.

At subsequent Step S12, the imaging distance estimating unit 110 estimates the imaging distance "r" to the mucosal surface 8 shown in the image. FIG. 4 is a flow chart illustrating in detail a process executed by the imaging distance estimating unit 110.

At Step S121, the low absorbance wavelength selecting unit 111 selects the low absorbance wavelength component, which is the wavelength component having the lowest degree of absorption or scattering in the living body. This is for suppressing influence of absorption or scattering of light by a blood vessel or the like near the mucosal surface 8 and for acquiring pixel values reflecting the imaging distance "r" between the endoscope 6 and the mucosal surface 8 most well. In an image composed of respective components of R, G, and B, the R-component is the most away from an absorption band of blood and is also the component of the longest wavelength, and thus is hard to be affected by the absorption or scattering in the living body. Therefore, in this first embodiment, the R-component is selected.

At subsequent Step S122, the imaging distance estimating unit 110 estimates, based on the R-component value selected as the low absorbance wavelength component, the imaging distance "r" when the mucosal surface 8 is assumed to be a uniform diffuser, by using next Equation (1).

$$r = \sqrt{\frac{I \times K \times \cos\theta}{L}} \quad (1)$$

In Equation (1), the symbol "I" is the emission power of a light source in the endoscope 6 and a measured value that has been measured beforehand is applied. The symbol "K" is a diffused reflection coefficient of the mucosal surface 8 and an average value is measured beforehand and applied. The symbol θ is an angle formed by a normal vector of the mucosal surface 8 and a vector from the mucosal surface 8 to the light source (endoscope 6). The angle θ is actually a value individually determined by a positional relation between the light source provided at a distal end of the endoscope 6 and the mucosal surface 8, but an average value is set beforehand and applied. The symbol "L" is the R-component value of a pixel having an estimation target region on the mucosal surface 8 at the imaging distance "r" taken therein.

Figure 5:
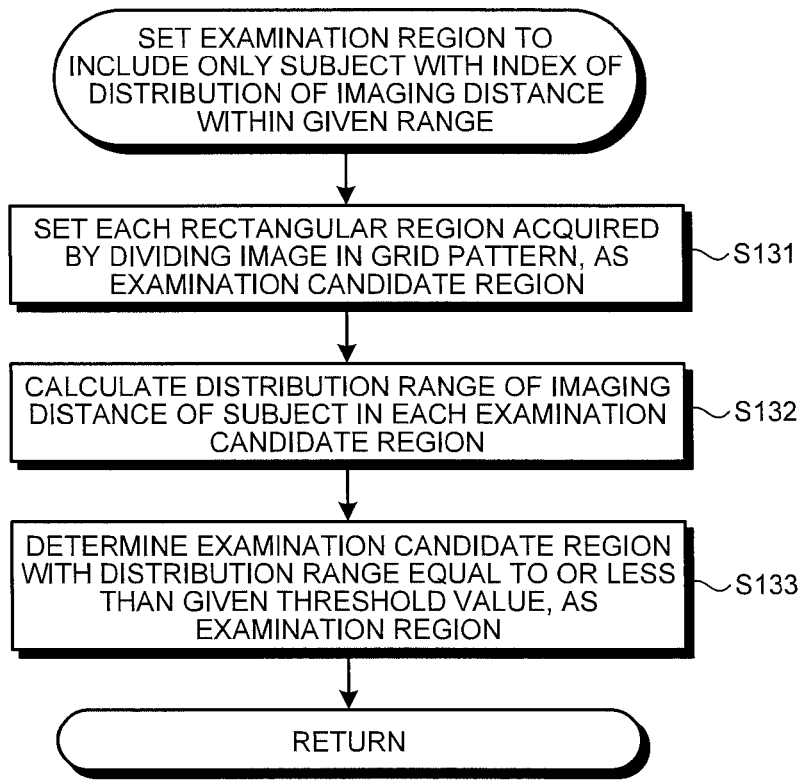
FIG. 5 is a flow chart illustrating in detail a process executed by an examination region setting unit illustrated in FIG. 1.

At Step S13 subsequent to Step S12, the examination region setting unit 120 sets an examination region in the image such that an index indicating a spread of a distribution of the imaging distance "r" of the subject shown in the examination region is within a given range. In this first embodiment, as the index indicating the spread of the distribution, a distribution range of the imaging distance "r" is used. FIG. 5 is a flow chart illustrating in detail a process executed by the examination region setting unit 120. Further, FIG. 6 is a schematic diagram illustrating the process executed by the examination region setting unit 120.

Figure 6:
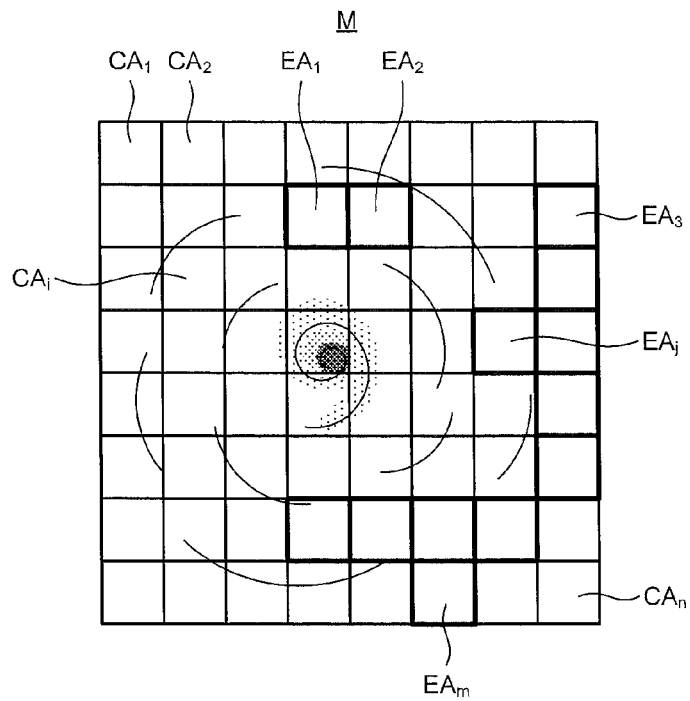
FIG. 6 is a schematic diagram illustrating a method of setting an examination region.

At Step S131, the candidate region setting unit 121 sets, as illustrated in FIG. 6, each of rectangular regions of a given size acquired by dividing the image "M" in a grid pattern, as an examination candidate region $CA_i$ (i=1, 2, ..., n).

At subsequent Step S132, the imaging distance range calculating unit 122a calculates the distribution range of the imaging distance "r" to the mucosal surface 8 shown in each examination candidate region $CA_i$. Specifically, in each examination candidate region $CA_i$, a difference $\Delta r$ ($\Delta r = r_{max} - r_{min}$) between the minimum value $r_{min}$ and the maximum value $r_{max}$ of the imaging distance "r" calculated from the R-component value of each pixel is found as the distribution range.

Further, at Step S133, the region determining unit 122 determines the examination candidate region with the distribution range $\Delta r$ equal to or less than a given threshold value to be an examination region. In this first embodiment, an examination region $EA_j$ (j=1, 2, ..., m; m≤n) illustrated by a bold frame in FIG. 6 is assumed to be determined.

Figure 7:
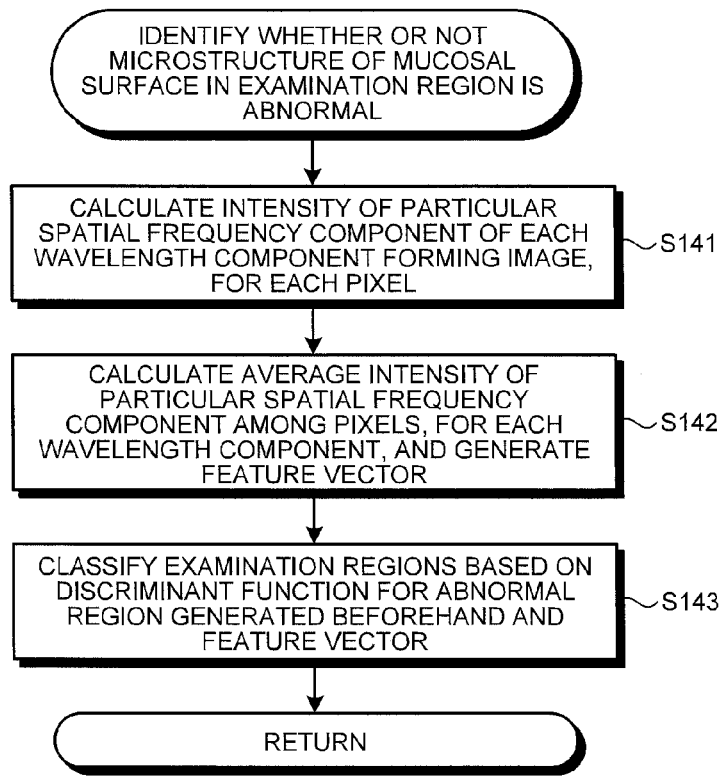
FIG. 7 is a flow chart illustrating in detail a process executed by an abnormal structure identifying unit illustrated in FIG. 1.

At Step S14 subsequent to Step S13, the abnormal structure identifying unit 130 identifies whether or not a surface of the subject shown in the determined examination region, that is, a microstructure of the mucosal surface 8, is abnormal. FIG. 7 is a flow chart illustrating in detail a process executed by the abnormal structure identifying unit 130.

At Step S141, the particular frequency component calculating unit 131 calculates, for each examination region $EA_j$, an intensity of a particular spatial frequency component of each of wavelength components (R-component, G-component, and B-component) forming the image "M", for each pixel. The particular spatial frequency component is a spatial frequency component enabling identification of presence or absence of an abnormality in the microstructure of the mucosal surface 8 shown in the image "M", and is set beforehand based on teacher data or the like.

Calculation of the particular spatial frequency component may be realized by applying a known band pass filter to each wavelength component of the examination region $EA_j$ (reference: "Digital Image Processing" by CG-ARTS Society, page 136 ("Band Pass Filter") and page 141 ("LOG Filter")).

In the first embodiment, band pass filtering (calculation of the particular spatial frequency component) is not performed with respect to pixels (end portion pixels) positioned at an end portion of the examination region $EA_j$. The reason for that is because if a particular spatial frequency component of an end portion pixel of the examination region $EA_j$ is calculated, a pixel outside the examination region $EA_j$ needs to be used, but like for the examination region $EA_3$, for example, if the examination region $EA_j$ is positioned at an end portion of the image "M", the outside of the examination region $EA_j$ is thus outside of the image "M" and there may be no pixels there. Further, even if there is a pixel outside the examination region $EA_j$, a value of that pixel outside the examination region $EA_j$ may be largely different from a pixel value of a pixel inside the examination region $EA_j$.

At Step S142, the statistical classification unit 132 calculates an average intensity of the particular spatial frequency component among the pixels in each examination region $EA_j$ for each wavelength component and generates a feature vector "x" having these average intensities as its components. In the first embodiment, calculation is performed with respect to the three wavelength components of R, G, and B, and thus the number of components of the feature vector "x" is three (that is, a matrix of three rows and one column).

If the microstructure of the mucosal surface is abnormal, a difference in intensity from that of a normal microstructure is generated, in a particular spatial frequency component of an intermediate band excluding a low frequency component representing a shape of the mucosal surface and a high frequency component representing imaging noise.

Therefore, at Step S143, the abnormal structure identifying unit 130 performs classification of whether or not each examination region $EA_j$ is an abnormal region based on a discriminant function for abnormal region generated beforehand and on the feature vector generated from the particular spatial frequency components. In an actual process, a classification index P(x) based on a probability model expressed by Equation (2) is calculated, and if this value is equal to or greater than a threshold value, that examination region EAj is classified as an abnormal region.

$$P(x) = \frac{1}{(2\pi)^{k/2} \times |Z|^{1/2}} \exp\left\{(x-\mu)^t \times \left(-\frac{1}{2}\right) Z^{-1} \times (x-\mu)\right\} \quad (2)$$

In Equation (2), the symbol μ is an average vector (three rows and one column) of feature vectors in samples of a plurality of abnormal regions acquired beforehand. The symbol "Z" is a variance-covariance matrix (three rows and three columns) in the samples of the plurality of abnormal regions acquired beforehand. The symbol |Z| is a determinant of the variance and covariance matrix. The symbol $Z^{-1}$ is an inverse matrix of the variance and covariance matrix. The symbol "k" is a dimensionality of the feature vector "x" and in the first embodiment, k=3.

In this first embodiment, the classification method for an abnormal region using the probability model has been described, but as long as classification of whether each examination region is abnormal or normal is possible, any method other than the one described above may be used. For example, classification may be performed by a method based on a feature space distance from a representative feature vector, a method of setting a classification boundary in a feature space, or the like.

At Step S15, the calculating unit 100 outputs a result of the abnormality identification in Step S14, causes the display unit 40 to display the result and the recording unit 50 to record the result. Thereafter, the process in the image processing apparatus 1 is ended.

As described above, according to the first embodiment, since the examination region is set in the image such that the index indicating the spread of the distribution of the imaging distance of the subject shown in the examination region is within the given range, and for each examination region, whether or not the microstructure of the subject shown in the examination region is abnormal is identified by using the particular spatial frequency component enabling identification of an abnormality in the microstructure of the subject shown in the examination region as the texture feature data; even if a difference in resolution with respect to a microstructure of a subject (mucosa) surface shown in an image is caused due to a difference in imaging distance, like, for example, between a distant view and a near view, an abnormality in a microstructure of a mucosal surface is able to be identified accurately.

Modified Example 1-1

Next, a modified example 1-1 of the first embodiment will be described.

Figure 8:
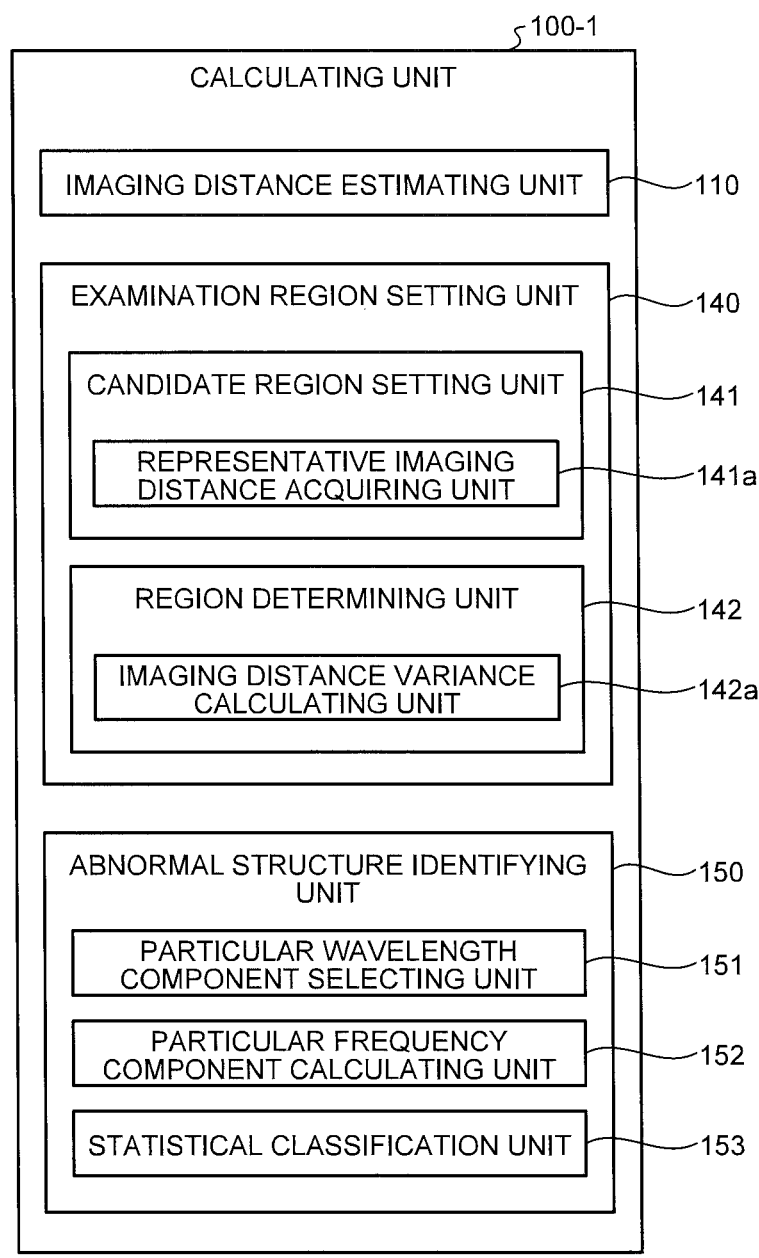
FIG. 8 is a block diagram illustrating a configuration of a calculating unit included in an image processing apparatus according to a modified example 1-1.

FIG. 8 is a block diagram illustrating a configuration of a calculating unit included in an image processing apparatus according to the modified example 1-1. As illustrated in FIG. 8, a calculating unit 100-1 according to the modified example 1-1 includes the imaging distance estimating unit 110, an examination region setting unit 140, and an abnormal structure identifying unit 150. The configuration and operations of the imaging distance estimating unit 110 are similar to those of the first embodiment. Further, the configuration and operations of the overall image processing apparatus other than the calculating unit 100-1 are similar to those of the first embodiment.

The examination region setting unit 140 includes a candidate region setting unit 141 and a region determining unit 142. Of these, the candidate region setting unit 141 includes a representative imaging distance acquiring unit 141a that acquires a representative imaging distance to a subject taken at a position where an examination candidate region is set, and the candidate region setting unit 141 sets the examination candidate region of a size corresponding to the representative imaging distance. Further, the region determining unit 142 includes an imaging distance variance calculating unit 142a that calculates a variance of the imaging distance to the subject shown in the examination candidate region, and the region determining unit 142 determines the examination candidate region with the variance equal to or less than a given threshold value to be an examination region.

The abnormal structure identifying unit 150 includes a particular wavelength component selecting unit 151 that selects a particular wavelength component specified according to a degree of absorption or scattering in a living body, a particular frequency component calculating unit 152 that calculates a particular frequency component at the selected wavelength, and a statistical classification unit 153 that performs statistical classification based on the particular spatial frequency component.

Next, operations of the calculating unit 100-1 will be described.

Figure 9:
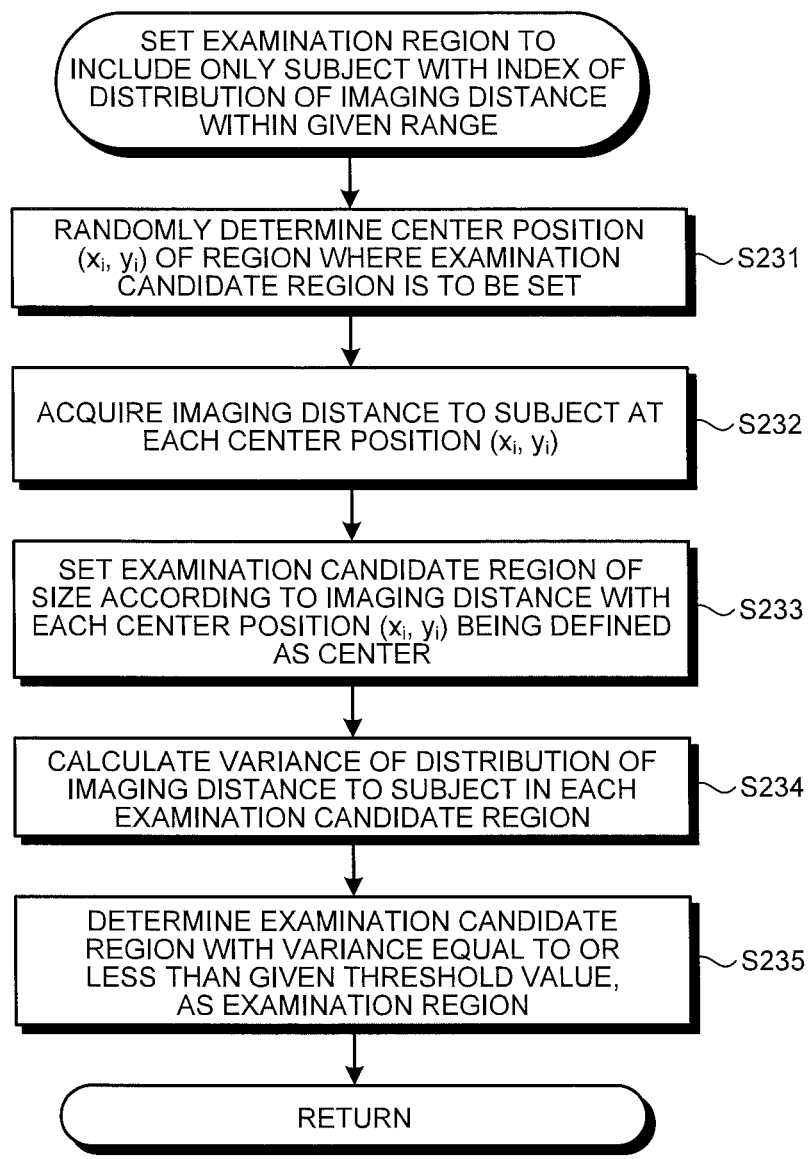
FIG. 9 is a flow chart illustrating in detail a process executed by an examination region setting unit illustrated in FIG. 8.
Figure 10:
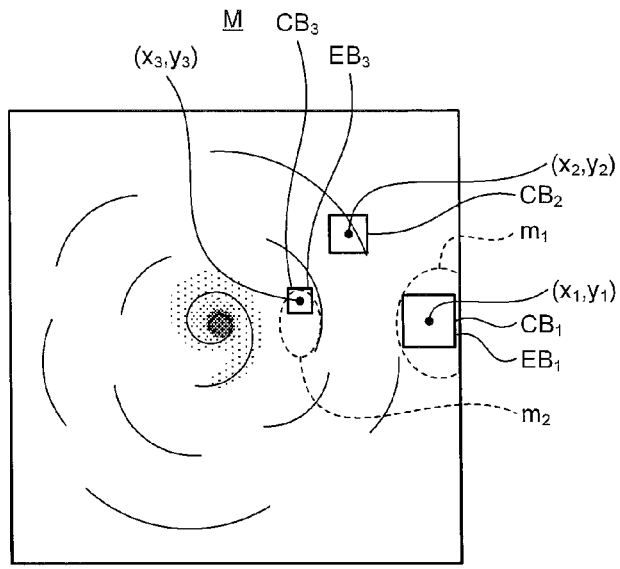
FIG. 10 is a schematic diagram illustrating the process executed by the examination region setting unit illustrated in FIG. 8.
Figure 11:
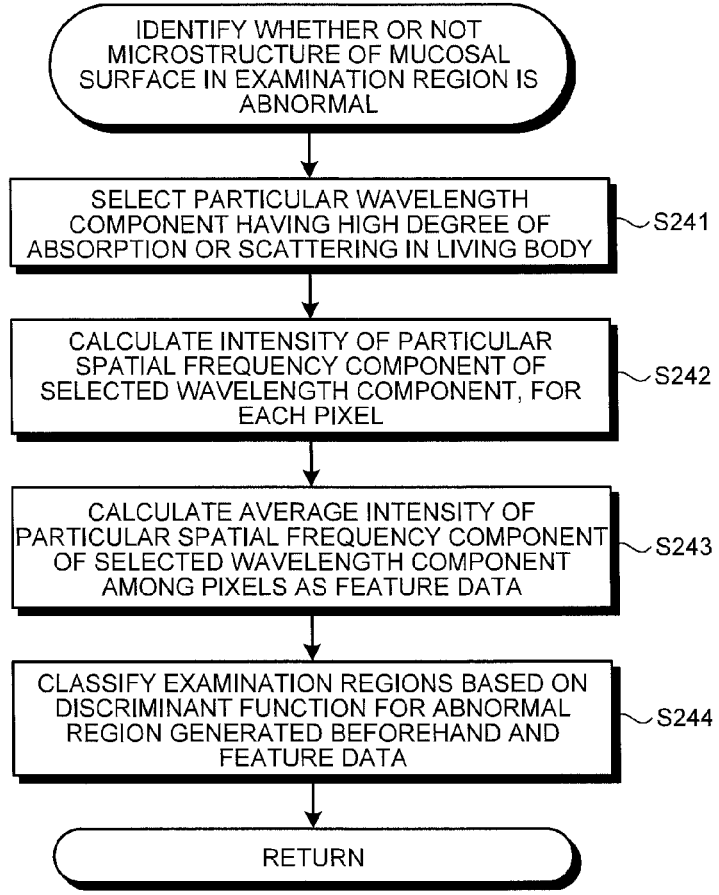
FIG. 11 is a flow chart illustrating in detail a process executed by an abnormal structure identifying unit illustrated in FIG. 8.

The operations of the calculating unit 100-1 as a whole are similar to those illustrated in FIG. 2 and the detailed processes in Steps S13 and S14 are different. FIG. 9 is a flow chart illustrating in detail a process (Step S13) executed by the examination region setting unit 140. FIG. 10 is a schematic diagram illustrating the process executed by the examination region setting unit 140. FIG. 11 is a flow chart illustrating in detail a process (Step S14) executed by the abnormal structure identifying unit 150.

At Step S13 subsequent to Step S12, the examination region setting unit 140 sets an examination region in the image "M" such that only a subject with an index indicating a spread of a distribution of imaging distance estimated in Step S12 within a given range is included therein. In this modified example 1-1, as the index indicating the spread of the distribution, rather than the distribution range of the imaging distance, a variance of the imaging distance, which is more stable against noise, will be used.

In more detail, as illustrated in FIG. 10, at Step S231, the candidate region setting unit 141 randomly determines a plurality of center positions $(x_i, y_i)$ (i=1, 2, . . . ) of regions where examination candidate regions are to be set. In FIG. 10, as an example, three center positions $(x_1, y_1)$, $(x_2, y_2)$ and $(x_3, y_3)$ are illustrated.

At subsequent Step S232, the representative imaging distance acquiring unit 141a acquires an imaging distance to the subject taken at each center position $(x_i, y_i)$. In an image, generally, a subject in a near view portion is taken largely and a subject in a distant view portion is taken small (see FIG. 3A). Therefore, if an examination region is set small as the imaging distance gets longer, a possibility of being able to suppress the variance of the imaging distance to the subject included in the examination region to be equal to or less than a given value is increased.

Thus, at Step S233, the candidate region setting unit 141 sets an examination candidate region $CB_i$ of a size according to the imaging distance with each center position $(x_i, y_i)$ being defined as the center thereof. The shape of the examination region is not particularly limited, and various shapes are applicable, such as a rectangular shape, and a circular shape. For example, in FIG. 10, for the center position $(x_1, y_1)$ of the near view portion, a comparatively large examination candidate region CB' is set, and for the center position $(x_3, y_3)$ of the distant view portion, a comparatively small examination candidate region $CB_3$ is set. Further, at the center position $(x_2, y_2)$ of the intermediate portion between these, an examination candidate region $CB_2$ of an intermediate size is set.

At Step S234, the imaging distance variance calculating unit 142a calculates a variance of a distribution of the imaging distance to the subject shown in each examination candidate region $CB_i$.

At Step S235, the region determining unit 142 determines the examination candidate region $CB_i$ with a variance equal to or less than a given threshold value to be an examination region $EB_i$. For example, in FIG. 10, the examination candidate regions $CB_1$ and $CB_3$ are determined to be examination regions $EB_1$ and $EB_3$.

At Step S14 subsequent to Step S13, the abnormal structure identifying unit 150 identifies whether or not a microstructure of a mucosal surface shown in the examination region $EB_i$ is abnormal. In the first embodiment, an abnormality in the microstructure is identified by using the particular spatial frequency components for all of wavelength components (R-component, G-component, and B-component). However, an abnormality in a microstructure of a mucosal surface is usually caused by a state of formation of the capillary vessels. Therefore, a wavelength component near the absorption band of blood demonstrates a prominent change. Accordingly, in this modified example 1-1, identification of an abnormal structure is performed by using, as the texture feature data, a particular spatial frequency component at a particular wavelength with a high degree of absorption or scattering in a living body.

In detail, at Step S241, the particular wavelength component selecting unit 151 selects, as the particular wavelength component having a high degree of absorption or scattering in the living body, for example, the G-component or the B-component.

At subsequent Step S242, the particular frequency component calculating unit 152 calculates, for each pixel, an intensity of the particular spatial frequency component at the selected wavelength component for each examination region $EB_i$. The particular spatial frequency component is set beforehand based on teacher data or the like.

At Step S243, the statistical classification unit 153 calculates an average intensity of the particular spatial frequency component of the selected wavelength component among the pixels and determines a value of this average intensity as feature data.

Further, at Step S244, the abnormal structure identifying unit 150 performs, based on a discriminant function for an abnormal region generated beforehand and the feature data, classification of whether or not each examination region $EB_i$ is an abnormal region. The process using the discriminant function is similar to that of the first embodiment. However, in a calculating formula of the classification index P(x) expressed by Equation (2), instead of the feature vector "x", the feature data calculated in Step S243 are applied. Further, instead of the average vector $\mu$ in Equation (2), an average value of feature data in samples of a plurality of samples of abnormal regions acquired beforehand is applied. Furthermore, instead of the variance-covariance matrix "Z" in Equation (2), a variance in the plurality of samples of abnormal regions acquired beforehand is applied, and instead of the inverse matrix $Z^{-1}$, a reciprocal of the variance in the samples is applied. Moreover, in Equation (2), k=1.

As described above, according to the modified example 1-1, since the size of the examination candidate region is changed according to the imaging distance, an examination region with an index indicating a spread of a distribution of imaging distance of a subject shown in the examination region within a given range is able to be set efficiently. As a result, identification of an abnormality in a microstructure for a mucosal surface of a wider range becomes possible and accuracy of the identification of an abnormality in a microstructure is able to be improved. In addition, by specifying the wavelength to be used in the identification of an abnormality in the microstructure, an abnormality in a microstructure accompanying absorption change is able to be identified accurately.

Modified Example 1-2

Next, a modified example 1-2 of the first embodiment will be described.

Figure 12:
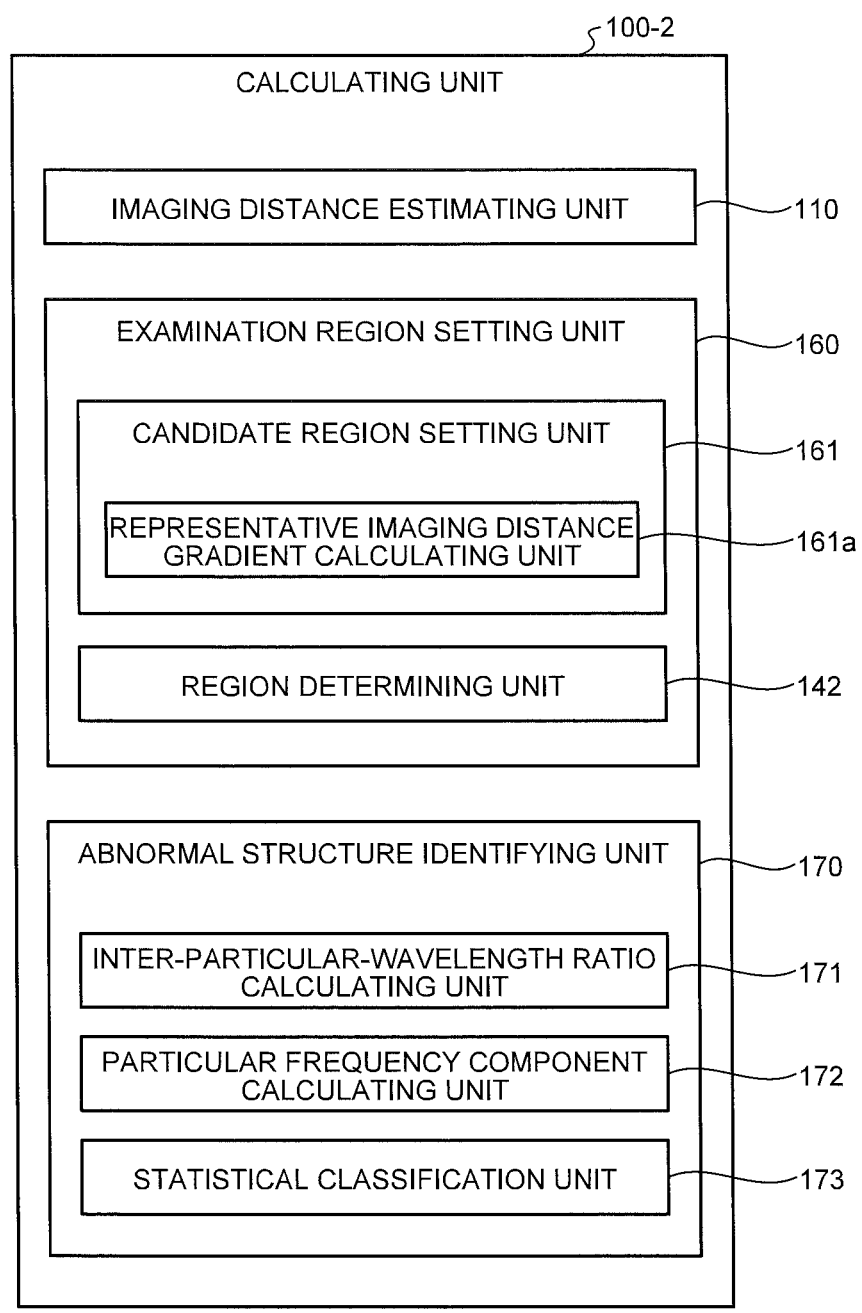
FIG. 12 is a block diagram illustrating a configuration of a calculating unit included in an image processing apparatus according to a modified example 1-2.

FIG. 12 is a block diagram illustrating a configuration of a calculating unit included in an image processing apparatus according to a modified example 1-2. As illustrated in FIG. 12, a calculating unit 100-2 according to the modified example 1-2 includes the imaging distance estimating unit 110, an examination region setting unit 160, and an abnormal structure identifying unit 170. The configuration and operations of the imaging distance estimating unit 110 are similar to those of the first embodiment. Further, the configuration and operations of the overall image processing apparatus other than the calculating unit 100-2 are similar to those of the first embodiment.

The examination region setting unit 160 includes a candidate region setting unit 161 and the region determining unit 142. The candidate region setting unit 161 includes a representative imaging distance gradient calculating unit 161a that calculates a representative imaging distance gradient of a subject taken at a position where an examination candidate region is to be set, and the candidate region setting unit 161 sets the examination candidate region of a size corresponding to the representative imaging distance gradient. The configuration and operations of the region determining unit 142 are similar to those of the modified example 1-1.

The abnormal structure identifying unit 170 includes an inter-particular-wavelength ratio calculating unit 171 that calculates a ratio between particular wavelength components having different degrees of absorption or scattering in a living body, a particular frequency component calculating unit 172 that calculates a particular spatial frequency component for the calculated ratio between the particular wavelength components, and a statistical classification unit 173 that performs statistical classification based on the particular spatial frequency component.

Next, operations of the calculating unit 100-2 will be described.

Figure 13:
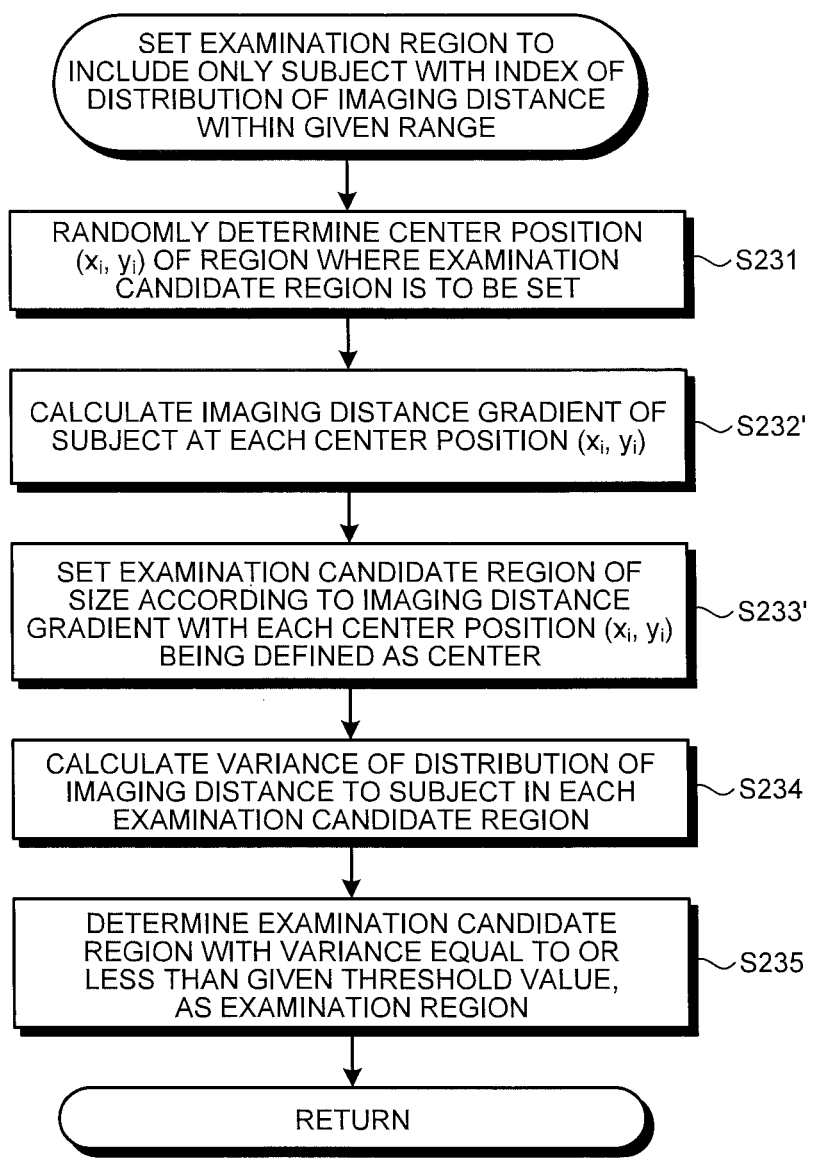
FIG. 13 is a flow chart illustrating in detail a process executed by an examination region setting unit illustrated in FIG. 12.
Figure 14:
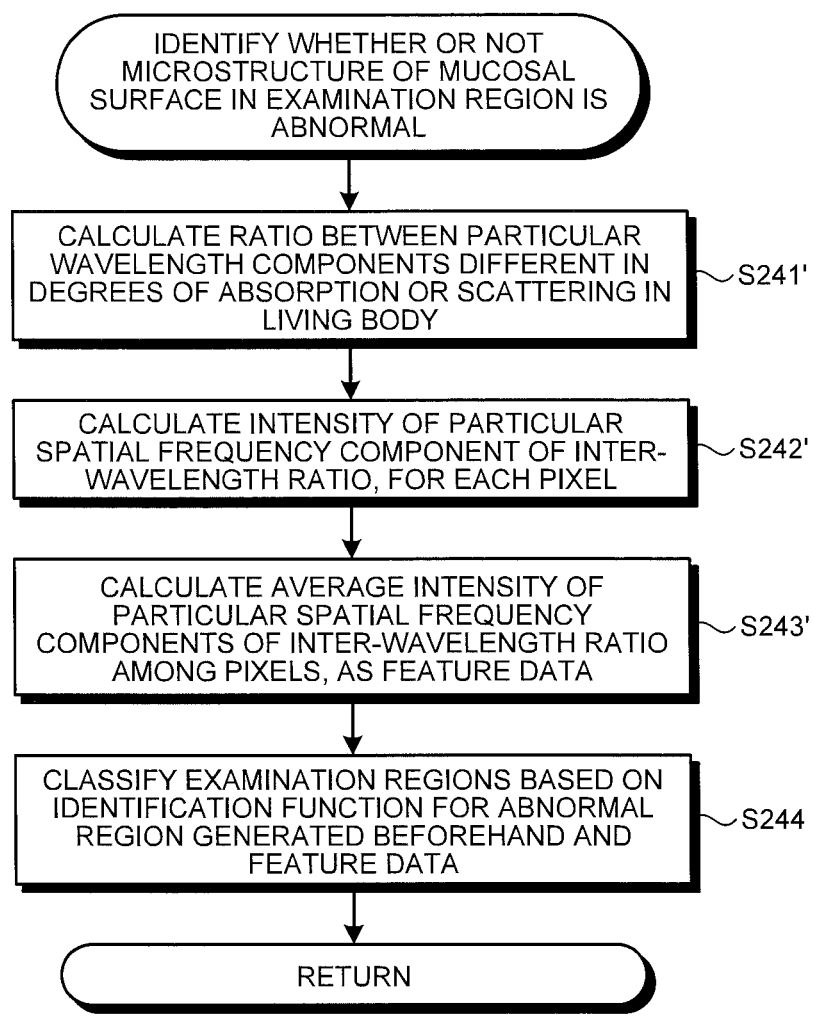
FIG. 14 is a flow chart illustrating in detail a process executed by an abnormal structure identifying unit illustrated in FIG. 12.

The operations of the calculating unit 100-2 as a whole are similar to those illustrated in FIG. 2 and the detailed processes in Steps S13 and S14 are different. FIG. 13 is a flow chart illustrating in detail a process (Step S13) executed by the examination region setting unit 160. FIG. 14 is a flow chart illustrating in detail a process (Step S14) executed by the abnormal structure identifying unit 170. Steps S231, S234, and S235 illustrated in FIG. 13 correspond to those illustrated in FIG. 9.

At Step S232' subsequent to Step S231 illustrated in FIG. 13, the representative imaging distance gradient calculating unit 161a calculates an imaging distance gradient of a subject taken at each center position $(x_i, y_i)$ determined randomly in the image "M" (see FIG. 10). In the actual process, a known one dimensional differential filter (reference: "Digital Image Processing" by CG-ARTS Society, page 114 ("Differential Filter")) is applied to the imaging distance of the subject taken at each pixel position to find an absolute value of the calculated value.

The larger the imaging distance gradient is, the larger the range of the imaging distance in a given region becomes. Therefore, if an examination region is set smaller as the imaging distance gradient at the position where an examination region is to be set gets larger, a possibility of being able to suppress the variance of the imaging distance to the subject included in the examination region to be equal to or less than a given value is increased.

Thus, at Step S233', the candidate region setting unit 161 determines a size of the examination candidate region according to the imaging distance gradient at each center position $(x_i, y_i)$ and sets an examination candidate region of the size according to the imaging distance gradient with each center position $(x_i, y_i)$ being defined as the center thereof.

Steps S234 and S235 thereafter are similar to those of the modified example 1-1.

At Step S14 subsequent to Step S13, the abnormal structure identifying unit 170 identifies whether or not a microstructure of a mucosal surface shown in the examination region is abnormal. In the modified example 1-1, an abnormality in the microstructure is identified by using the particular spatial frequency component at the particular wavelength with a high degree of absorption or scattering in the living body. However, the pixel value change in a microstructure shown in an image is influenced by the imaging distance, and in the distant view portion, the change is small, and in the near view portion, the change is large. Therefore, the average intensity of the particular spatial frequency component calculated in the modified example 1-1 includes the pixel value change corresponding to the imaging distance and if identification of an abnormal structure by using the same discriminant function is performed, there is a possibility that the identification accuracy may be reduced. Accordingly, in this modified example 1-2, in order to suppress the influence by the pixel value change associated with the imaging distance, a ratio between particular wavelength components having degrees of absorption or scattering in a living body different from each other is calculated, and an abnormal structure is identified by using, as the texture feature data, a particular spatial frequency component at that ratio.

In detail, at Step S241' illustrated in FIG. 14, the inter-particular-wavelength ratio calculating unit 171 calculates, based on a pixel value of each pixel in an examination region, for example, G/R or the like, as the ratio between the particular wavelength components with the degrees of absorption or scattering in the living body different from each other. Hereinafter, the ratio calculated thereby will be referred to as "inter-wavelength ratio".

At subsequent Step S242', the particular frequency component calculating unit 172 calculates, for each pixel in each examination region, an intensity of the particular spatial frequency component of the inter-wavelength ratio. The particular spatial frequency component is set beforehand based on teacher data or the like.

At Step S243', the statistical classification unit 173 calculates an average intensity of the particular spatial frequency component of the inter-wavelength ratio among the pixels, and determines a value of this average intensity as feature data.

Further, at Step S244, the abnormal structure identifying unit 170 performs, based on a discriminant function for an abnormal region generated beforehand and the feature data, classification of whether or not each examination region is an abnormal region. The details of this process are similar to those of the modified example 1-1.

As described above, according to the modified example 1-2, because the size of the examination region is changed according to the imaging distance gradient at the position where the examination region is to be set, an examination region with an index indicating a spread of a distribution of imaging distance within a given range is able to be set efficiently. As a result, identification of an abnormality in a microstructure for a mucosal surface of a wider range becomes possible and accuracy of the identification of an abnormality in the microstructure is able to be improved. Further, by using the inter-wavelength ratio upon the identification of an abnormality in the microstructure, an intensity change of a particular spatial frequency component caused according to imaging distance is able to be suppressed, and an abnormality in a microstructure is able to be identified accurately.

Second Embodiment

Next, a second embodiment of the present invention will be described.

Figure 15:
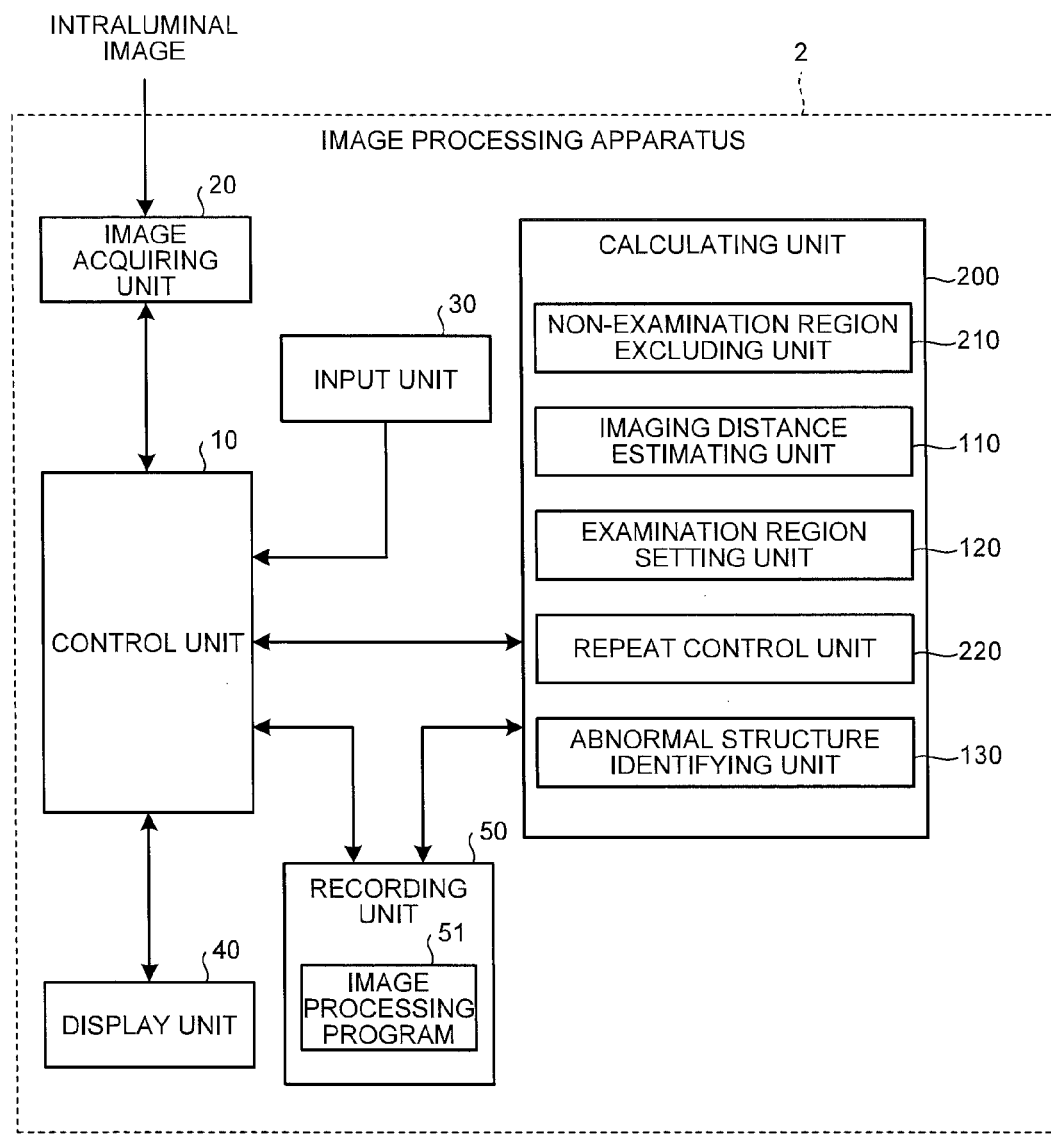
FIG. 15 is a block diagram illustrating a configuration of an image processing apparatus according to a second embodiment of the present invention.

FIG. 15 is a block diagram illustrating a configuration of an image processing apparatus according to the second embodiment of the present invention. As illustrated in FIG. 15, an image processing apparatus 2 according to the second embodiment includes a calculating unit 200, instead of the calculating unit 100 illustrated in FIG. 1. The configurations and operations of the respective units of the image processing apparatus 2 other than the calculating unit 200 are similar to those of the first embodiment.

The calculating unit 200 includes: a non-examination region excluding unit 210 that excludes, from a target to be processed, a region (non-examination target region) not to be identified for an abnormality in the image; the imaging distance estimating unit 110; the examination region setting unit 120; a repeat control unit 220 that performs control of causing setting of an examination region for a region where an examination region has not been set to be repeatedly executed; and the abnormal structure identifying unit 130. Of these, the configurations and operations of the imaging distance estimating unit 110, the examination region setting unit 120, and the abnormal structure identifying unit 130 are similar to those of the first embodiment. Instead of the examination region setting unit 120 and the abnormal structure identifying unit 130, the examination region setting unit 140 and the abnormal structure identifying unit 150 according to the modified example 1-1 or the examination region setting unit 160 and the abnormal structure identifying unit 170 according to the modified example 1-2 may be applied.

Figure 16:
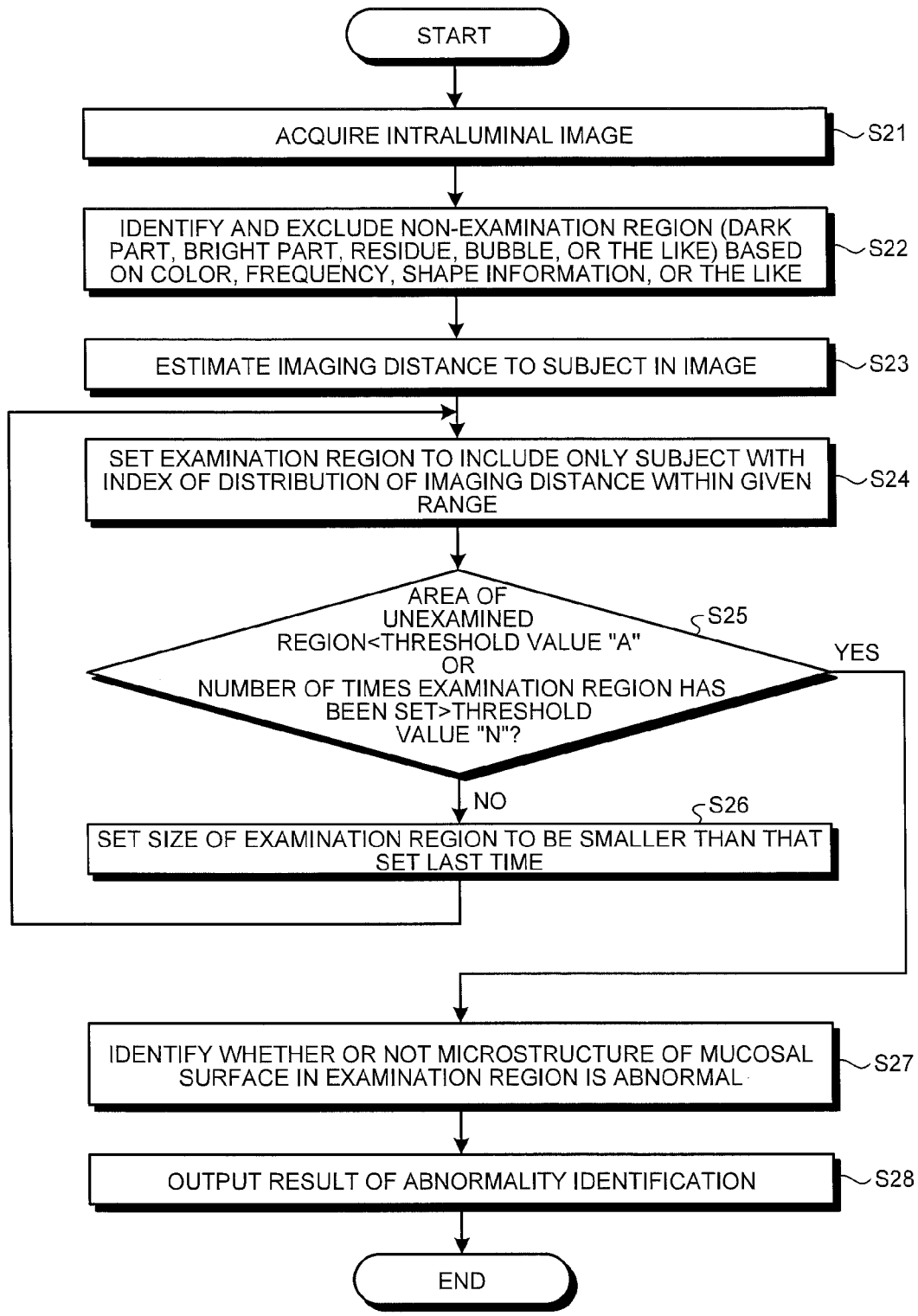
FIG. 16 is a flow chart illustrating operations of the image processing apparatus illustrated in FIG. 15.

Next, operations of the image processing apparatus 2 will be described. FIG. 16 is a flow chart illustrating the operations of the image processing apparatus 2.

First, at Step S21, the calculating unit 200 reads the image data recorded in the recording unit 50 to thereby acquire an intraluminal image to be processed.

At subsequent Step S22, the non-examination region excluding unit 210 identifies, based on color information, frequency information, shape information, and the like acquirable from the image, a non-examination region, such as a dark part, a bright part, a residue, a bubble, or the like, and excludes the non-examination region from the examination target.

An intraluminal image contains, other than a mucosa region to be examined, a region where a deep part of a lumen is shown (dark part), a halation region which is mirror-reflected from a surface of a subject (bright part), a region where a residue or a bubble is shown, and the like. If these regions are included in an examination region, accuracy of identification of an abnormality in a microstructure is reduced. Thus, the non-examination region excluding unit 210 extracts, from the image, a region where a bright part, a dark part, a residue, a bubble, or the like is shown and excludes the region as a non-examination region. These non-examination regions may be extracted by various known methods. For example, a dark part may be extracted by extracting a black region, based on color feature data that is based on color information (respective values of R-component, G-component, and B-component, or the like) of each pixel in an image, and identifying, based on a direction of a pixel value change around this black region, whether or not the black region is a dark part (reference: Japanese Patent Application Laid-open No. 2011-234931). Further, a bright part may be extracted, for example, by extracting a white region, based on the color feature data of each pixel in the image, and identifying, based on a pixel value change around a boundary of this white region, whether or not the white region is a halation region (same as above). A residue may be extracted by detecting, based on the color feature data of each pixel in the image, a residue candidate region likely to be a non-mucosa region, and identifying, based on a positional relation between this residue candidate region and a structural edge in the image, whether or not the residue candidate region is a mucosa region. A bubble may be extracted by extracting an edge from the image and calculating a correlation value between a bubble model set beforehand based on a feature of a bubble image and the extracted edge (reference: Japanese Patent Application Laid-open No. 2007-313119).

At Step S23, the imaging distance estimating unit 110 estimates an imaging distance to a subject shown in the image. This estimating process is similar to that of the first embodiment (see Step S12 of FIG. 2).

At Step S24, the examination region setting unit 120 sets an examination region in the image such that an index indicating a spread of a distribution of imaging distance of the subject shown in the examination region is within a given range. This process of setting the examination region is similar to that of the first embodiment (see Step S13 of FIG. 2).

At Step S25, the repeat control unit 220 determines whether an area of an unexamined region, which is a region where an examination region has not been set yet, is smaller than a given threshold value (threshold value "A") or whether or not the number of times an examination region has been set so far is larger than a given threshold value (threshold value "N"). If examination regions in an image have not been set sufficiently, there is a possibility that accuracy of identification of an abnormality in a microstructure may be reduced. Accordingly, if the area of the unexamined region is equal to or greater than the threshold value "A" and the number of times an examination region has been set is equal to or less than the threshold value "N" (Step S25: No), the repeat control unit 220 determines that setting of an examination region is needed further, and sets the size of an examination region to be smaller than that set last time (Step S26). The repeat control unit 220 proceeds to Step S24 and causes the examination region setting unit 120 to execute the setting of an examination region again. By decreasing the size of an examination region like this, a range of imaging distance included in one examination region is often narrowed, and thus a possibility of regions settable as examination regions being increased in an image becomes higher.

On the contrary, if the area of the unexamined region is less than the threshold value "A" or the number of times an examination region has been set is greater than the threshold value "N" (Step S25: Yes), the repeat control unit 220 determines that further setting of an examination region is not necessary, proceeds to Step S27, and causes the abnormal structure identifying unit 130 to execute identification of an abnormality in a microstructure. This process of identifying an abnormality in the microstructure is similar to that of the first embodiment (see Step S14 of FIG. 2).

Further, at Step S28, the calculating unit 200 outputs a result of the abnormality identification (see Step S15 of FIG. 2).

As described above, according to the second embodiment, since the examination region is set by excluding the non-examination region beforehand, an abnormality in a microstructure is able to be identified accurately. Further, by repeating the setting of an examination region, identification of an abnormality in a microstructure for a mucosal surface of a wider range becomes possible and accuracy of the identification of an abnormality in the microstructure is able to be improved. Further, by decreasing the size of an examination region every time the process is repeated, an abnormality in a microstructure is able to be identified for a mucosal surface of a wider range and accuracy of the identification of an abnormality in the microstructure is able to be improved.

Third Embodiment

Next, a third embodiment of the present invention will be described.

Figure 17:
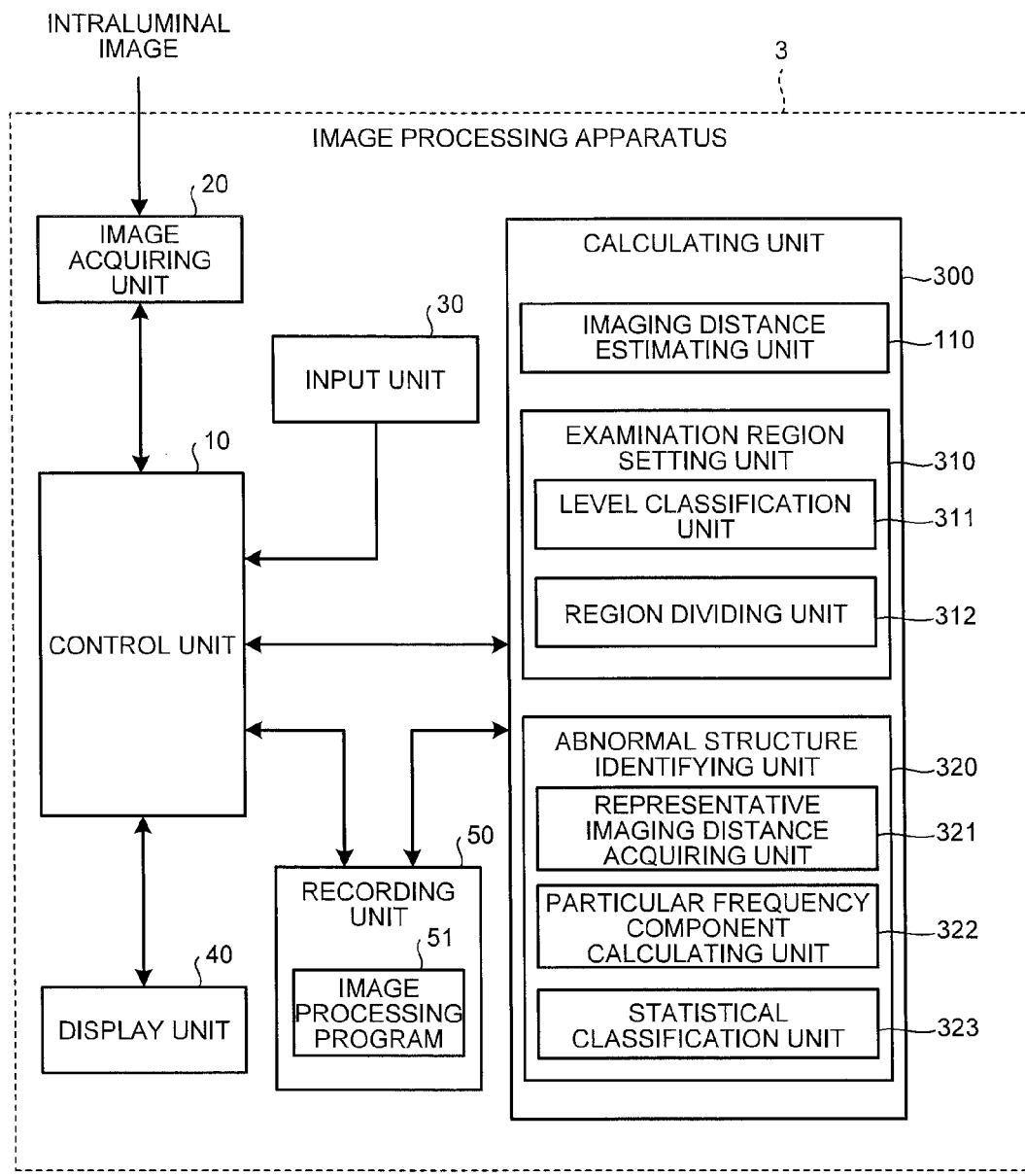
FIG. 17 is a block diagram illustrating a configuration of an image processing apparatus according to a third embodiment of the present invention.

FIG. 17 is a block diagram illustrating a configuration of an image processing apparatus according to the third embodiment of the present invention. As illustrated in FIG. 17, an image processing apparatus 3 according to the third embodiment includes a calculating unit 300, instead of the calculating unit 100 illustrated in FIG. 1. The configurations and operations of the respective units of the image processing apparatus 3 other than the calculating unit 300 are similar to those of the first embodiment.

The calculating unit 300 includes the imaging distance estimating unit 110, an examination region setting unit 310, and an abnormal structure identifying unit 320. Of these, the configuration and operations of the imaging distance estimating unit 110 are similar to those of the first embodiment.

The examination region setting unit 310 includes a level classification unit 311 that classifies values of imaging distance into one level or a plurality of levels; a region dividing unit 312 that divides, for each region where the subject at imaging distance classified into the same level is shown, the image into one region or a plurality of regions, and the examination region setting unit 310 sets each of the one region or plurality of regions acquired by the region dividing unit 312 as an individual examination region.

The abnormal structure identifying unit 320 includes a representative imaging distance acquiring unit 321 that acquires a representative imaging distance to a subject shown in an examination region, a particular frequency component calculating unit 322 that calculates a particular spatial frequency component according to the representative imaging distance, and a statistical classification unit 323 that performs statistical classification, based on the particular spatial frequency component.

Next, operations of the image processing apparatus 3 will be described.

Figure 18:
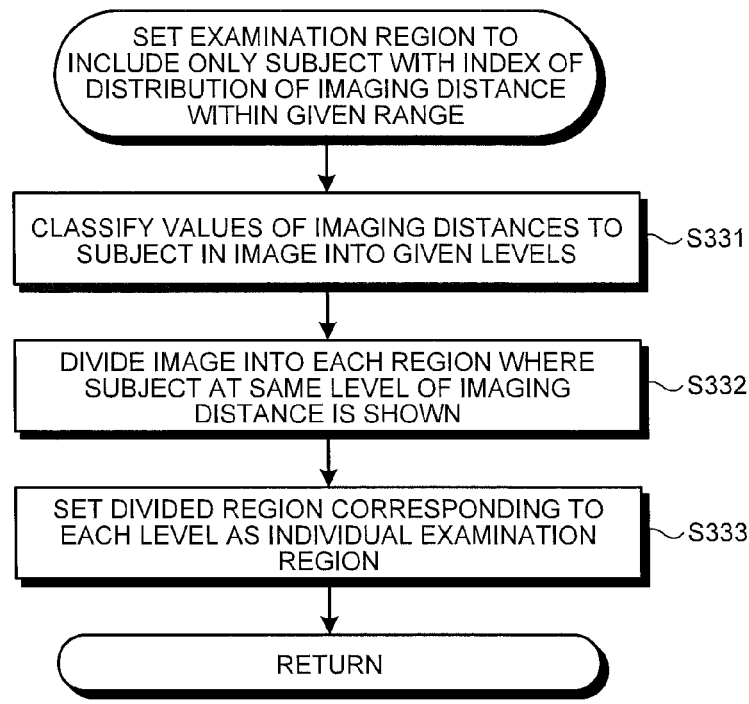
FIG. 18 is a flow chart illustrating in detail a process executed by an examination region setting unit illustrated in FIG. 17.
Figure 19:
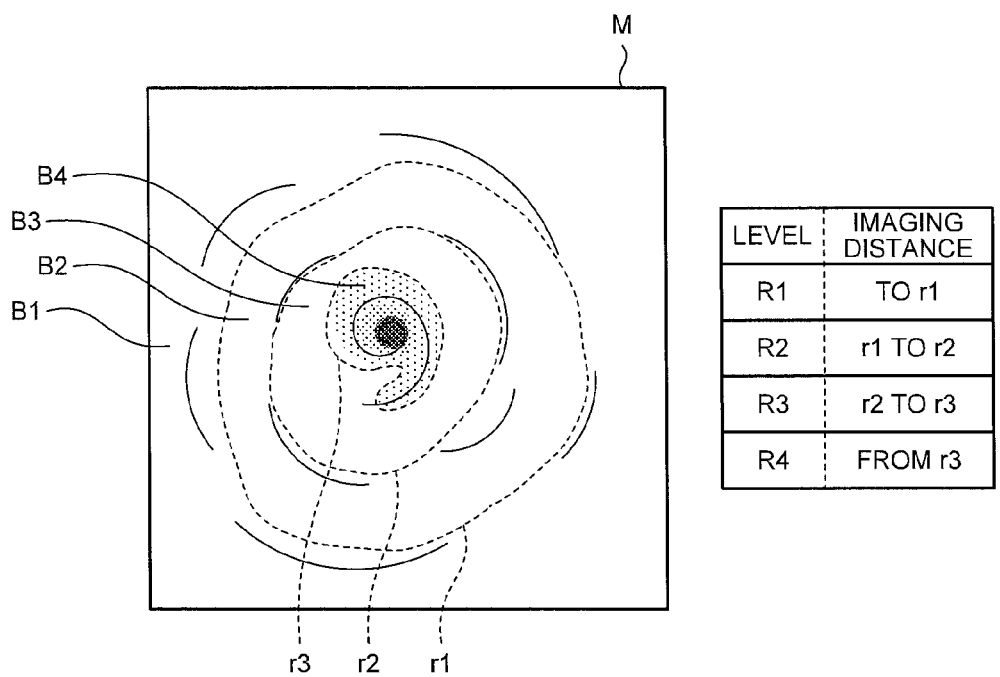
FIG. 19 is a schematic diagram illustrating the process executed by the examination region setting unit illustrated in FIG. 17.
Figure 20:
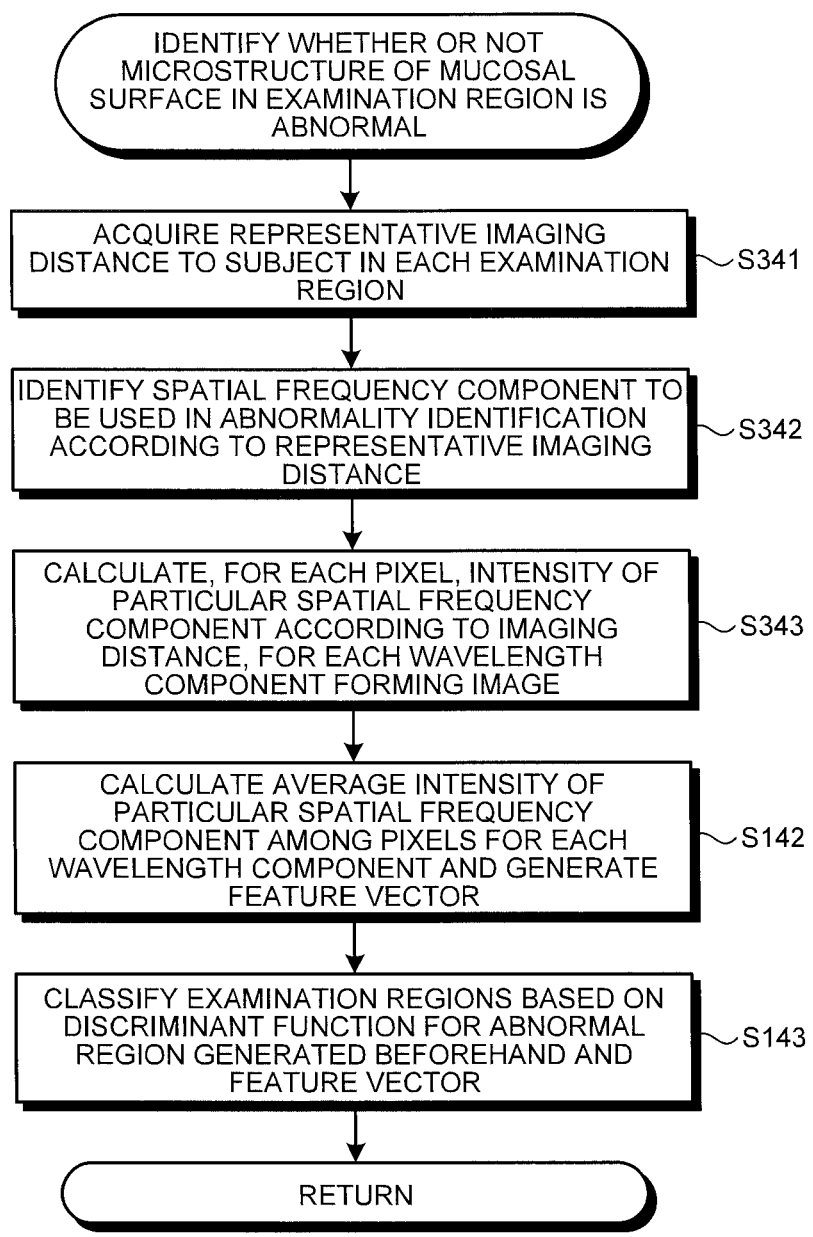
FIG. 20 is a flow chart illustrating in detail a process executed by an abnormal structure identifying unit illustrated in FIG. 17.
Figure 21:
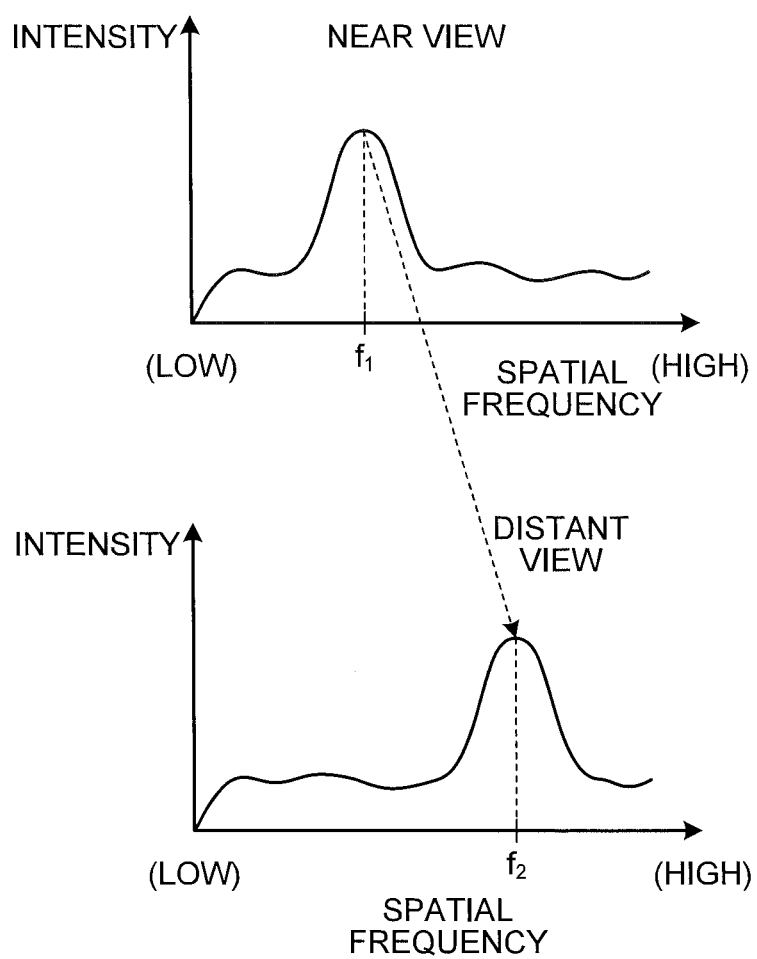
FIG. 21 is a schematic diagram illustrating intensity characteristics of frequency components according to imaging distance in an intraluminal image.

The operations of the image processing apparatus 3 as a whole are similar to those illustrated in FIG. 2 and the detailed processes at Steps S13 and S14 are different. FIG. 18 is a flow chart illustrating in detail a process (Step S13) executed by the examination region setting unit 310. FIG. 19 is a schematic diagram illustrating the process executed by the examination region setting unit 310. FIG. 20 is a flow chart illustrating in detail a process (Step S14) executed by the abnormal structure identifying unit 320. FIG. 21 is a schematic diagram illustrating intensity characteristics of frequency components according to imaging distance in an intraluminal image.

At Step S13 subsequent to Step S12, the examination region setting unit 310 sets an examination region in the image "M" such that an index indicating a spread of a distribution of imaging distance of a subject shown in the examination region is within a given range.

In detail, first, at Step S331 illustrated in FIG. 18, the level classification unit 311 classifies values of the imaging distances to the subject shown in the image "M" into a plurality of given levels. Each level is set such that a range of the imaging distance is equal to or less than a given value.

At subsequent Step S332, the region dividing unit 312 divides the image "M" into each region where the subject at the same level of imaging distance is shown. For example, in FIG. 19, the image "M" is divided into four divided regions B1 to B4 correspondingly with a level R1 where the imaging distance is equal to or less than r1, a level R2 where the imaging distance is in a range of r1 to r2, a level R3 where the imaging distance is in a range of r2 to r3, and a level R4 where the imaging distance is equal to or greater than r3.

At Step S333, the examination region setting unit 310 sets the divided regions B1 to B4 corresponding to the respective levels R1 to R4 as individual examination regions.

At Step S14 subsequent to Step S13, the abnormal structure identifying unit 320 identifies whether or not a microstructure of a mucosal surface shown in the examination region is abnormal.

In detail, at Step S341 illustrated in FIG. 20, the representative imaging distance acquiring unit 321 acquires a representative imaging distance to the subject in each of the examination regions (divided regions) B1 to B4. Examples of the representative imaging distance include an average value of the imaging distances to the subject included in the examination regions B1 to B4 or an imaging distance at coordinates of gravity center of the examination regions B1 to B4.

At subsequent Step S342, the particular frequency component calculating unit 322 identifies, for each of the examination regions B1 to B4, according to the representative imaging distance, a spatial frequency component to be used in identification of an abnormality. As described above, in an intraluminal image captured by an endoscope, different resolutions of a microstructure of a mucosal surface are obtained according to the imaging distance. Specifically, the longer the imaging distance is, the lower the resolution becomes. Therefore, for example, as illustrated in FIG. 21, if the imaging distance is short (near view) and a particular spatial frequency enabling identification of an abnormality in a microstructure is $f_1$, a spatial frequency enabling identification of an abnormality in the same microstructure shifts to a higher frequency side as the imaging distance gets longer (distant view: spatial frequency $f_2$).

Accordingly, in this third embodiment, according to the representative imaging distance of each of the examination regions B1 to B4, a particular spatial frequency component to be used as texture feature data upon identification of an abnormality in a microstructure is changed, in order to achieve improvement in accuracy of the identification and increase in the efficiency of the process. Specifically, the longer the imaging distance is, the higher the particular spatial frequency component is made, to thereby enable detection for a finer structure. The shorter the imaging distance is, the lower the particular spatial frequency component is made, to thereby suppress the amount of calculation. The particular spatial frequency component according to the imaging distance is set beforehand based on teacher data or the like.

At Step S343, the particular frequency component calculating unit 322 calculates, for each pixel in each of the examination regions B1 to B4, an intensity of the particular spatial frequency component according to the imaging distance for each wavelength component forming the image. The process of calculating the intensity of the particular spatial frequency component is similar to that of the first embodiment (see Step S141 of FIG. 7).

Subsequent Steps S142 and S143 are similar to those of the first embodiment.

As described above, according to the third embodiment, without repeating the process of setting or determining an examination candidate region or the like, an examination region over a wide range in an image is able to be set efficiently. As a result, accurate identification of an abnormality in a microstructure becomes possible. Further, since the spatial frequency component to be used in the identification of an abnormality in a microstructure is specified based on the representative imaging distance to the subject shown in the examination region, accurate identification of an abnormality in a microstructure becomes possible regardless of imaging distance and efficiency of the calculation process is able to be increased.

Fourth Embodiment

Next, a fourth embodiment of the present invention will be described.

Figure 22:
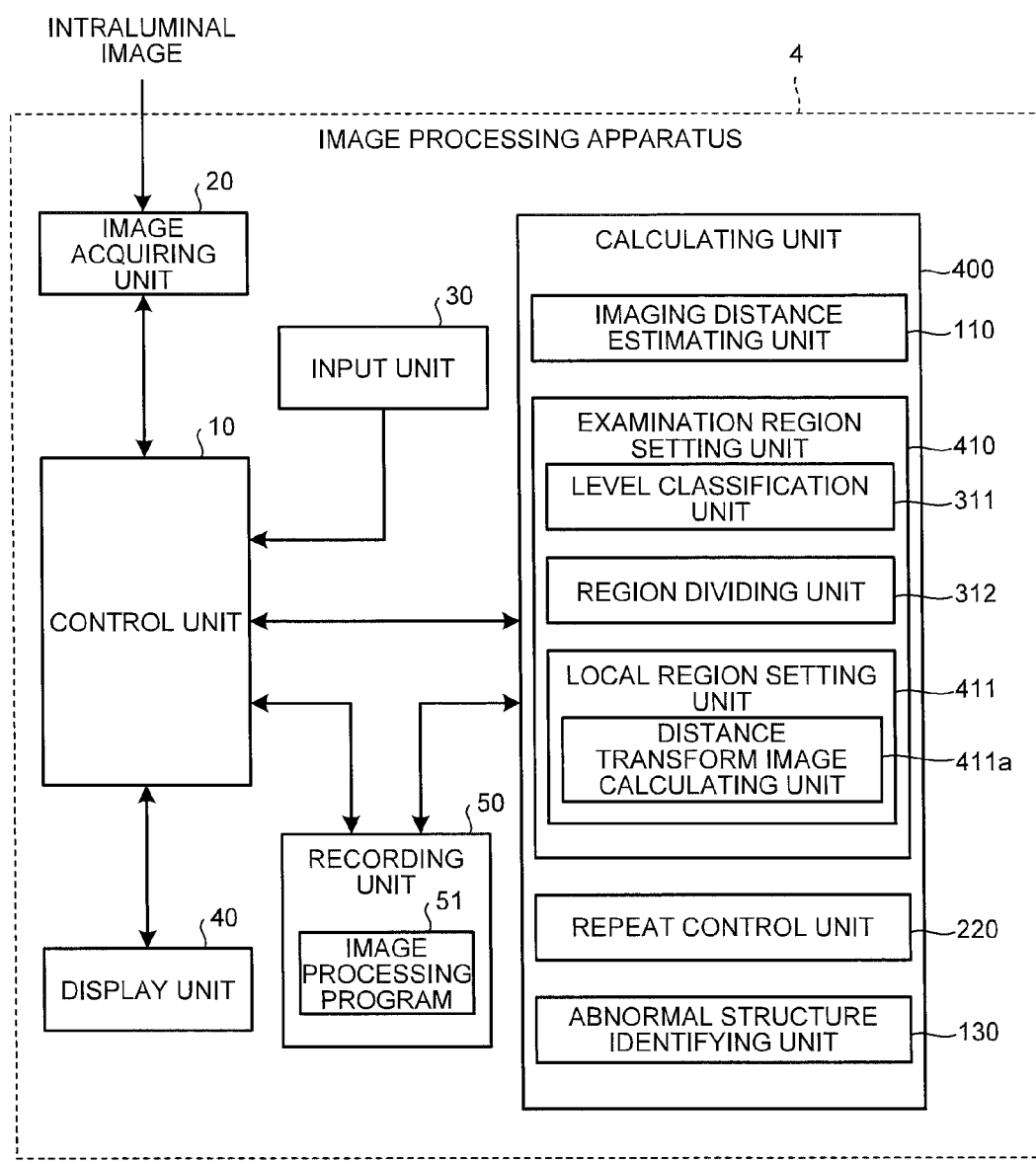
FIG. 22 is a block diagram illustrating a configuration of an image processing apparatus according to a fourth embodiment of the present invention.

FIG. 22 is a block diagram illustrating a configuration of an image processing apparatus according to the fourth embodiment of the present invention. As illustrated in FIG. 22, an image processing apparatus 4 according to the fourth embodiment includes a calculating unit 400, instead of the calculating unit 100 illustrated in FIG. 1. The configurations and operations of the respective units of the image processing apparatus 4 other than the calculating unit 400 are similar to those of the first embodiment.

The calculating unit 400 includes the imaging distance estimating unit 110, an examination region setting unit 410, the repeat control unit 220, and the abnormal structure identifying unit 130. Of these, the configurations and operations of the imaging distance estimating unit 110 and the abnormal structure identifying unit 130 are similar to those of the first embodiment.

The examination region setting unit 410 includes the level classification unit 311, the region dividing unit 312, and a local region setting unit 411. Of these, the configurations and operations of the level classification unit 311 and the region dividing unit 312 are similar to those of the third embodiment.

The local region setting unit 411 sets a local region in a region where a subject at the same level of imaging distance classified by the level classification unit 311 is shown. In more detail, the local region setting unit 411 includes a distance transform image calculating unit 411a that calculates a distance transform image acquired by transforming distances from a boundary of the region where the subject at the imaging distance classified in the same level is shown into pixel values, and the local region setting unit 411 sets the local region based on the distance transform image.

Next, operations of the image processing apparatus 4 will be described.

Figure 23:
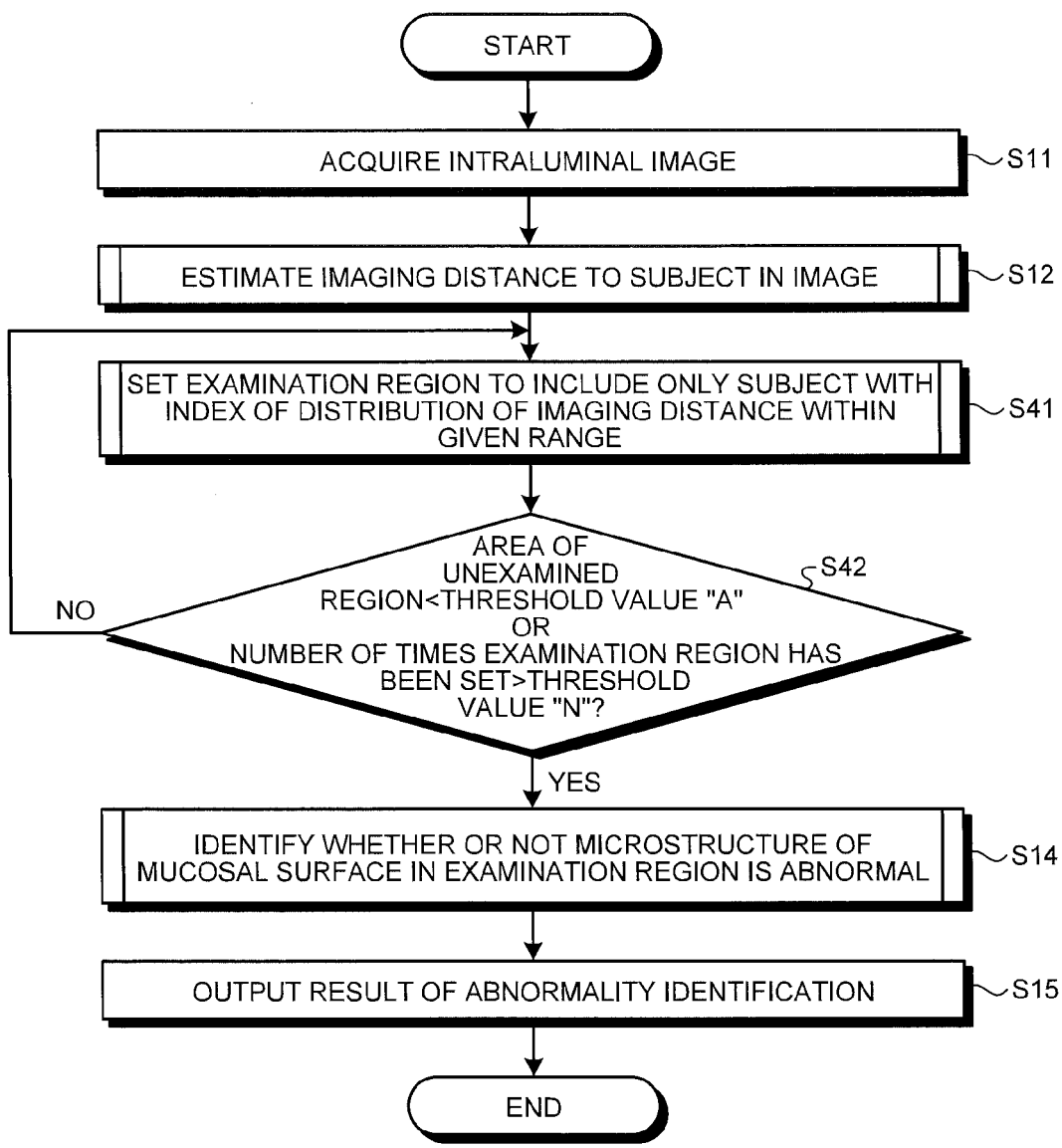
FIG. 23 is a flow chart illustrating operations of the image processing apparatus illustrated in FIG. 22.

FIG. 23 is a flow chart illustrating the operations of the image processing apparatus 4. Steps S11, S12, S14, and S15 illustrated in FIG. 23 correspond to those of the first embodiment (see FIG. 2).

Figure 24:
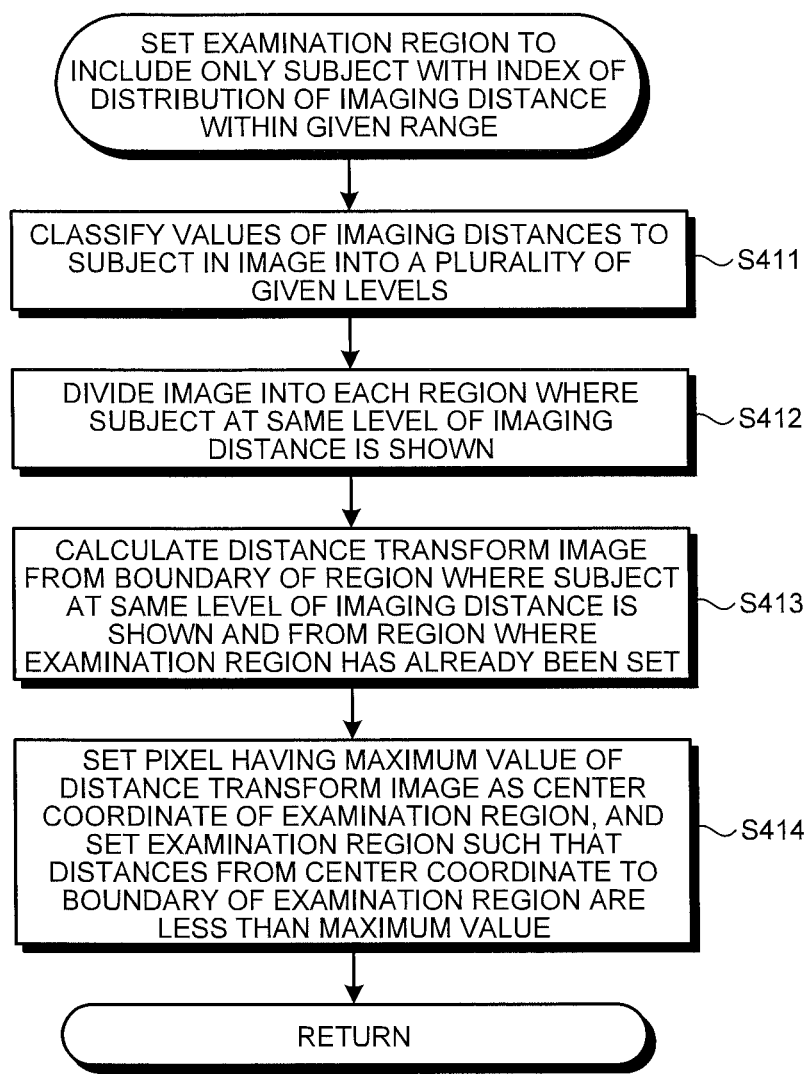
FIG. 24 is a flow chart illustrating in detail a process executed by an examination region setting unit illustrated in FIG. 22.
Figure 25:
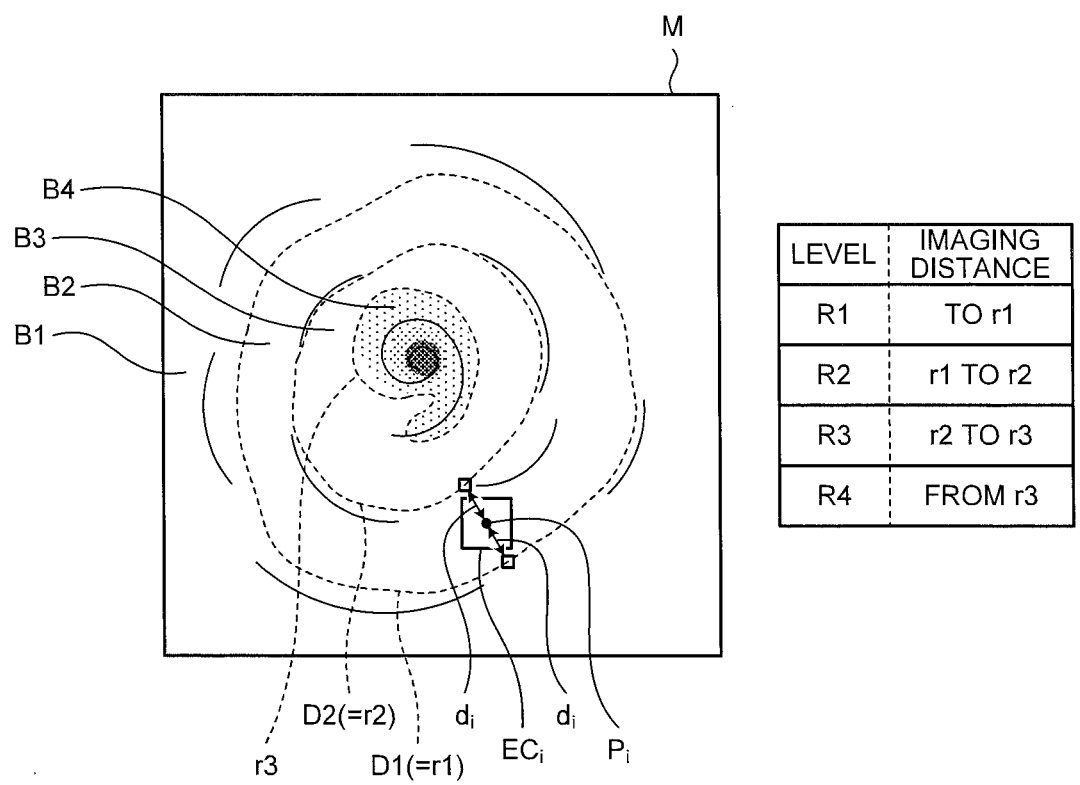
FIG. 25 is a schematic diagram illustrating the process executed by the examination region setting unit illustrated in FIG. 22.

At Step S41 subsequent to Step S12, the examination region setting unit 410 sets an examination region in an image such that an index indicating a spread of a distribution of imaging distance of a subject shown in the examination region is within a given range. FIG. 24 is a flow chart illustrating in detail a process executed by the examination region setting unit 410. Further, FIG. 25 is a schematic diagram illustrating the process executed by the examination region setting unit 410.

At Step S411, the level classification unit 311 classifies values of the imaging distances to the subject shown in the image "M" into a plurality of given levels.

At subsequent Step S412, the region dividing unit 312 divides the image "M" into each region where the subject at the same level of imaging distance is shown. Thereby, for example, in FIG. 25, the image "M" is divided into the four divided regions B1 to B4 correspondingly with the level R1 where the imaging distance is equal to or less than r1, the level R2 where the imaging distance is in the range of r1 to r2, the level R3 where the imaging distance is in the range of r2 to r3, and the level R4 where the imaging distance is equal to or greater than r3.

Each of the divided regions B1 to B4 divided like this has an arbitrary shape according to the subject in the image "M". Therefore, if these divided regions B1 to B4 are directly set as examination regions to execute a process of calculating particular spatial frequency components as texture feature data, the necessity of determining whether or not the entire pixels of rectangular regions including the examination regions are of examination regions for which the particular spatial frequency components are to be calculated is created, and a long period of time is required in that process. Therefore, in the fourth embodiment, based on the divided regions B1 to B4, an examination region is set for a local region in a region where a target at the same level of imaging distance is shown.

In detail, at Step S413, the distance transform image calculating unit 411a calculates a distance transform image from a boundary of the region where the subject at the same level of imaging distance is shown and from a region where an examination region has been already set.

At subsequent Step S414, the local region setting unit 411 sets an examination region such that a pixel having a maximum value of values in the distance transform image is a center coordinate of the examination region and distances from the center coordinate to an end of the examination region are less than the maximum value. The pixel having the maximum value of values in the distance transform image is any one of pixels at midpoints with equal distances from two boundaries, and for example, in FIG. 25, a pixel $P_i$ positioned at a midpoint between a boundary D1 and a boundary D2 of the divided region B2 corresponding to the level R2 corresponds to that pixel. In that case, the maximum value of the values of the distance transform image is a distance $d_i$ to the boundary D1 or D2 from the pixel $P_i$. With the pixel $P_i$ at the center, an examination region $EC_i$ with the maximum value of the diagonal line not exceeding a distance of $d_i \times 2$ is set. Thereby, in a region where a subject at the same level of imaging distance is shown, a rectangular examination region is able to be set.

At Step S42 subsequent to Step S41, the repeat control unit 220 determines whether or not an area of an unexamined region is less than the threshold value "A" or whether or not the number of times an examination region has been set so far is greater than the threshold value "N". The reason for performing this determination is because if examination regions have not been set sufficiently in an image, there is a possibility that accuracy of identification of an abnormality in a microstructure may be reduced.

If the area of the unexamined region is equal to or greater than the threshold value "A" and the number of times an examination region has been set is equal to or less than the threshold value "N" (Step S42: No), the repeat control unit 220 determines that further setting of an examination region is needed, proceeds to Step S41, and causes the examination region setting unit 410 to execute the setting of an examination region again. On the contrary, if the area of the unexamined region is less than the threshold value "A" or if the number of times an examination region has been set is greater than the threshold value "N" (Step S42: Yes), the process proceeds to Step S14.

As described above, according to the fourth embodiment, without repeating a process of setting and determining an examination candidate region or the like, an examination region enabling efficient execution of calculation of a particular spatial frequency component is able to be set. Therefore, the overall process of identifying an abnormality in a microstructure is able to be speeded up.

Fifth Embodiment

Next, a fifth embodiment of the present invention will be described.

Figure 26:
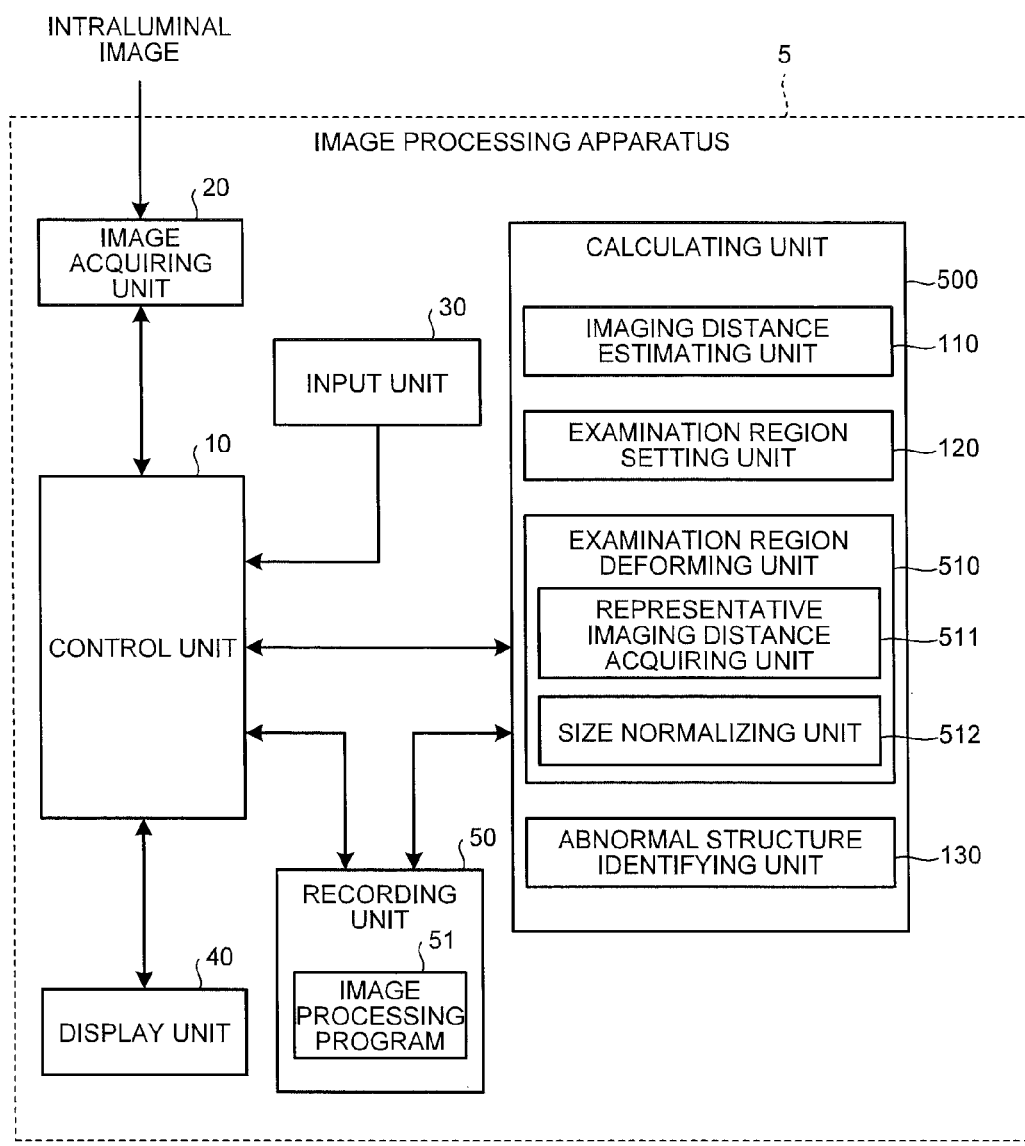
FIG. 26 is a block diagram illustrating a configuration of an image processing apparatus according to a fifth embodiment of the present invention.

FIG. 26 is a block diagram illustrating a configuration of an image processing apparatus according to the fifth embodiment of the present invention. As illustrated in FIG. 26, an image processing apparatus 5 according to the fifth embodiment includes a calculating unit 500, instead of the calculating unit 100 illustrated in FIG. 1. The configurations and operations of the respective units of the image processing apparatus 5 other than the calculating unit 500 are similar to those of the first embodiment.

The calculating unit 500 includes the imaging distance estimating unit 110, the examination region setting unit 120, an examination region deforming unit 510 that deforms an image in an examination region, and the abnormal structure identifying unit 130. Of these, the configurations and operations of the imaging distance estimating unit 110, the examination region setting unit 120, and the abnormal structure identifying unit 130 are similar to those of the first embodiment.

The examination region deforming unit 510 includes a representative imaging distance acquiring unit 511 that acquires a representative imaging distance to a subject shown in an examination region and a size normalizing unit 512 that normalizes a size of the examination region according to the representative imaging distance.

Next, operations of the image processing apparatus 5 will be described.

Figure 27:
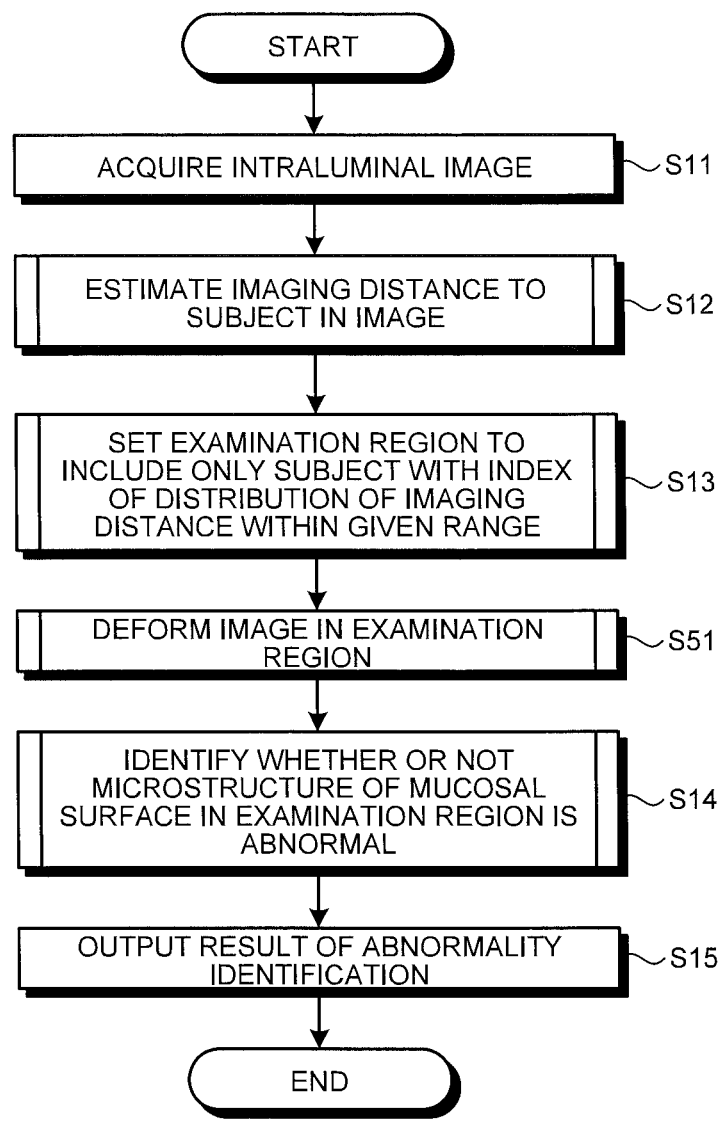
FIG. 27 is a flow chart illustrating operations of the image processing apparatus illustrated in FIG. 26.

FIG. 27 is a flow chart illustrating the operations of the image processing apparatus 5. Steps S11 to S15 illustrated in FIG. 27 correspond to those of the first embodiment (see FIG. 2).

At Step S51 subsequent to Step S13, the examination region deforming unit 510 deforms the image in the examination region. As described above, in an intraluminal image captured by an endoscope, resolutions of a microstructure of a mucosal surface differ according to the imaging distance. Accordingly, in this fifth embodiment, according to the imaging distance to the set examination region, the image in the examination region is deformed, and a particular spatial frequency component in the deformed image is used as texture feature data to identify an abnormality in a microstructure, to thereby improve the identification accuracy.

Figure 28:
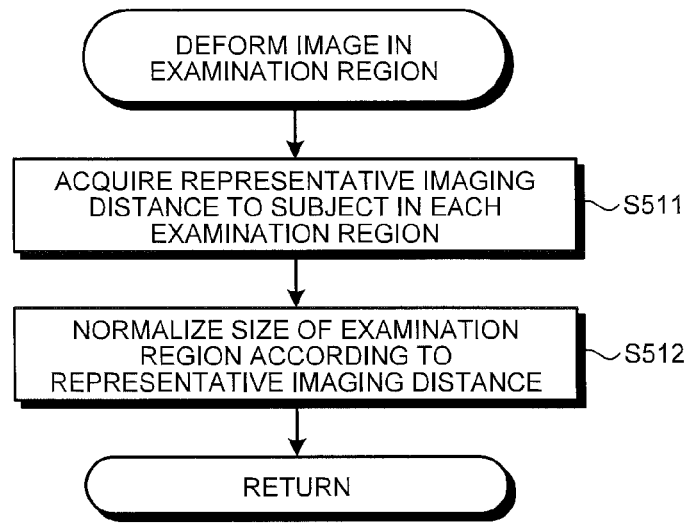
FIG. 28 is a flow chart illustrating in detail a process executed by an examination region deforming unit illustrated in FIG. 26.
Figure 29:
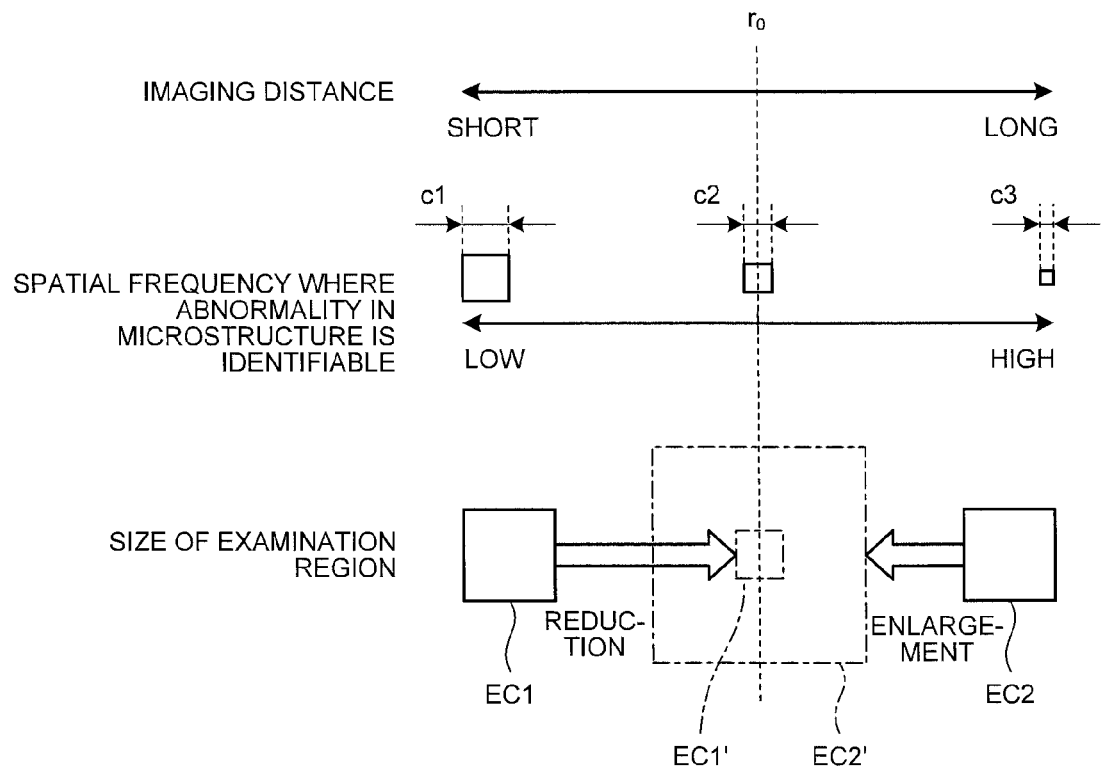
FIG. 29 is a schematic diagram illustrating a concept of the process executed by the examination region deforming unit illustrated in FIG. 26.

FIG. 28 is a flow chart illustrating in detail a process (Step S51) executed by the examination region deforming unit 510. Further, FIG. 29 is a schematic diagram illustrating a concept of the process executed by the examination region deforming unit 510.

First, at Step S511, the representative imaging distance acquiring unit 511 acquires a representative imaging distance to a subject shown in each examination region.

At subsequent Step S512, the size normalizing unit 512 normalizes a size of the examination region according to the representative imaging distance. As illustrated in FIG. 29, at a certain imaging distance $r_0$, a cycle of a pixel value change corresponding to particular spatial frequency enabling identification of an abnormality in a microstructure is assumed to be $c_2$. As compared to this imaging distance $r_0$, as the imaging distance becomes shorter, the particular spatial frequency shifts to a low frequency side and the cycle of the pixel value change becomes larger ($c_1 > c_2$). On the contrary, as compared to this imaging distance $r_0$, as the imaging distance becomes longer, the particular spatial frequency shifts to a high frequency side and the cycle of the pixel value change becomes smaller ($c_3 < c_2$).

Accordingly, as compared to the imaging distance $r_0$, if the imaging distance of an examination region EC1 to be processed is shorter (that is, for a near view portion), by reducing the examination region EC1 according to the ratio between the cycles $c_1$ and $c_2$, a resolution of the reduced examination region EC1' is able to be made equal to that for the imaging distance $r_0$. On the contrary, as compared to the imaging distance $r_0$, if the imaging distance of an examination region EC2 to be processed is longer (that is, for a distant view portion), by enlarging the examination region EC2 according to the ratio between the cycles $c_2$ and $c_3$, a resolution of the enlarged examination region EC2' is able to be made equal to that for the imaging distance $r_0$. That is, by performing such deforming, at later Step S14, regardless of the imaging distance of the examination region, the same particular spatial frequency component is able to be calculated to perform identification of an abnormality.

As described above, according to the fifth embodiment, by normalizing, based on the representative imaging distance to the subject shown in the examination region, the size of the examination region, regardless of imaging distance, by calculating the same particular spatial frequency, an abnormality in a microstructure is able to be identified accurately.

Modified Example 5-1

Next, a modified example 5-1 of the fifth embodiment will be described.

Figure 30:
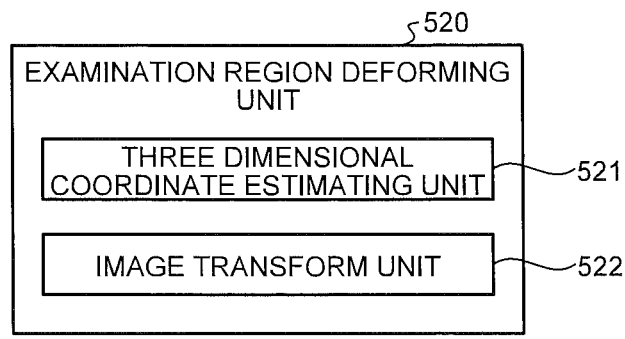
FIG. 30 is a block diagram illustrating a configuration of an examination region deforming unit according to a modified example 5-1.

FIG. 30 is a block diagram illustrating a configuration of an examination region deforming unit according to the modified example 5-1. A calculating unit according to the modified example 5-1 includes an examination region deforming unit 520 illustrated in FIG. 30, instead of the examination region deforming unit 510 illustrated in FIG. 26. This examination region deforming unit 520 includes a three dimensional coordinate estimating unit 521 that estimates three dimensional coordinates, based on the imaging distance and coordinates in the image, for at least three reference points on a subject shown in an examination region, and an image transform unit 522 that performs image transform on the examination region such that the examination region is transformed into an image acquired when the examination region in a plane spanned by the at least three reference points is directly oppositely imaged from a given distance.

Operations of the calculating unit according to the modified example 5-1 as a whole are similar to those illustrated in FIG. 27 and the process at Step S51 is different from that of the fifth embodiment.

Figure 31:
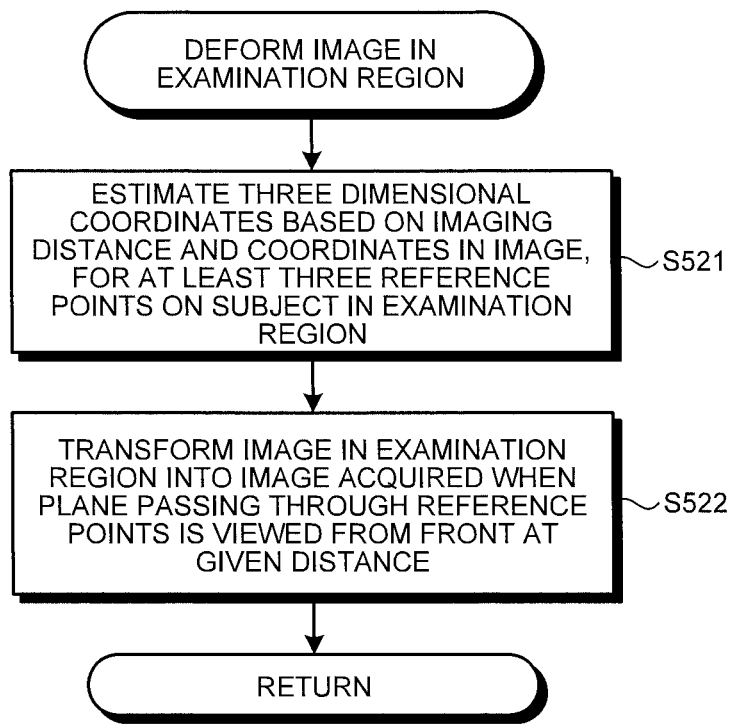
FIG. 31 is a flow chart illustrating in detail a process executed by the examination region deforming unit illustrated in FIG. 30.
Figure 32A:
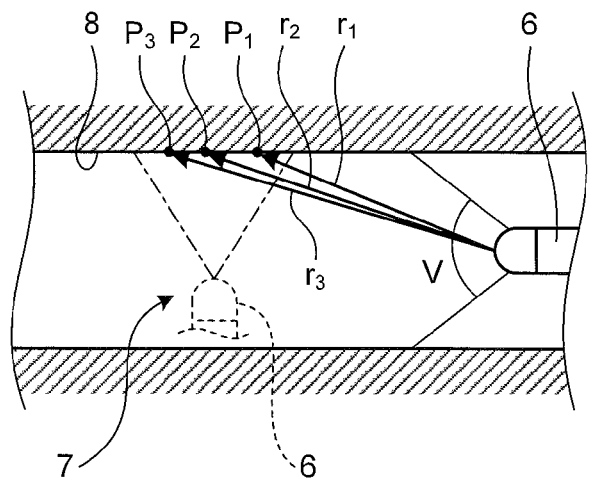
FIG. 32A is a schematic diagram illustrating a concept of the process executed by the examination region deforming unit illustrated in FIG. 30.
Figure 32B:
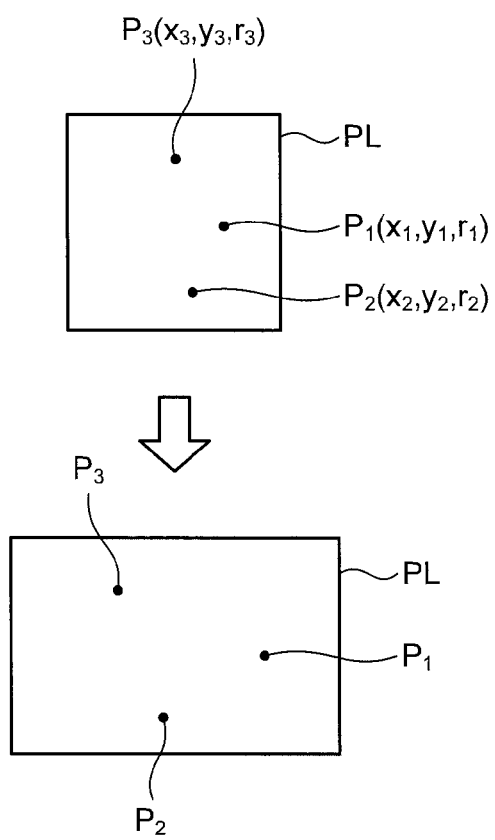
FIG. 32B is a schematic diagram illustrating the process executed by the examination region deforming unit illustrated in FIG. 30.

FIG. 31 is a flow chart illustrating details of a process (Step S51) executed by the examination region deforming unit 520. Further, FIG. 32A and FIG. 32B are schematic diagrams illustrating a concept of the process executed by the examination region deforming unit 520.

At Step S51 subsequent to Step S13, the examination region deforming unit 520 deforms an image in the examination region. Although in the fifth embodiment, the size of the examination region is normalized, a difference in imaging distance within a given range remaining in the examination region is not corrected, and influence is generated due to a difference between a resolution of the microstructure of the mucosal surface with a short imaging distance and a resolution of the microstructure of the mucosal surface with a long imaging distance in the same examination region. Therefore, in this modified example 5-1, as illustrated in FIG. 32A, an examination region is deformed as if a region including three reference points (for example, points $P_1$, $P_2$, and $P_3$) on the mucosal surface 8 in the lumen 7 has been imaged by the endoscope 6 from the front.

In detail, at Step S521, the three dimensional coordinate estimating unit 521 estimates three dimensional coordinates, based on the imaging distance and coordinates in the image, for the at least three reference points on the subject shown in the examination region. In the actual process, arbitrary three pixels away from one another in the examination region are selected first. Then, as illustrated in FIG. 32B, for example, based on imaging distances $r_1$, $r_2$, and $r_3$ to positions (reference points) $P_1$, $P_2$, and $P_3$ on the subject corresponding to these pixels, a focal distance of the imaging device (for example, the endoscope 6), and coordinates $(x_1, y_1)$, $(x_2, y_2)$, and $(x_3, y_3)$ in the image corresponding to the positions $P_1$, $P_2$, and $P_3$, three dimensional coordinates of the positions $P_1$, $P_2$, and $P_3$ on the subject in a coordinate system with the origin being the imaging device are estimated. The focal distance of the imaging device is determined beforehand.

At subsequent Step S522, the image transform unit 522 performs image transform on the examination region such that the examination region becomes an image acquired when a region on the subject in the examination region is imaged from the front at a given distance. This image transform may be executed by supposing, for example, that transform is performed to an image captured at a given focal distance while placing a viewpoint at a position away by a given distance towards a normal direction of a plane PL passing through the positions $P_1$, $P_2$, and $P_3$ on the subject from gravity centers of the positions $P_1$, $P_2$, and $P_3$ on the plane PL (or gravity centers of regions on the subject corresponding to the examination regions).

As described above, according to the modified example 5-1, a difference in imaging distance in an examination region is able to be corrected. That is, in a transformed image, a variation in distance between each position in a region on a subject corresponding to each pixel position in the same examination region and a position of an imaging device is able to be decreased from that in the image that has not been transformed. Thereby, a difference between a resolution of a microstructure of a mucosal surface with a near imaging distance and a resolution of the microstructure of the mucosal surface with a distant imaging distance in the same examination region is able to be decreased. Therefore, by using, as texture feature data, a particular spatial frequency component in an image transformed as above, accuracy of identification of an abnormality in a microstructure is able to be improved further.

As described above, according to the first to fifth embodiments and their modified examples, since the examination region is set in the image such that the index indicating the spread of the distribution of the imaging distance of the subject shown in the examination region is within the given range, and the texture feature data allowing identification of an abnormality in the microstructure of the subject shown in the examination region are used for each examination region, to thereby identify whether or not the microstructure of the subject shown in the examination region is abnormal, even if a difference is caused in resolution of a microstructure of a mucosal surface shown in an image due to a difference in imaging distance, an abnormality in the microstructure of the mucosal surface is able to be identified accurately.

In the above described first to fifth embodiments and their modified examples, as an example of the texture feature data, the spatial frequency component numerically expressing the frequency characteristics of the texture is used, but statistical feature data of the texture may be used instead. The statistical feature data of the texture may be found by using a co-occurrence matrix of pixel values. Specifically, by a co-occurrence matrix, from values of a pixel pair at two positions away from each other in an image, statistics (feature data) representing characteristics, such as uniformity, directionality, contrast, and the like of the pixel values are able to be found (reference: "Digital Image Processing" by CG-ARTS Society, pages 194 to 195 ("Texture of Region")).

The image processing apparatuses according to the above described first to fifth embodiments and their modified examples may be realized by executing an image processing program recorded in a recording device by a computer system, such as a personal computer or a work station. Further, such a computer system may be used by being connected to another computer system or a device, such as a server, via a local region network/wide area network (LAN/WAN), or a public network, such as the Internet. In this case, the image processing apparatuses according to the first to third embodiments may acquire image data of intraluminal images via these networks, output image processing results to various output devices (such as viewers and printers) connected via these networks, or store the image processing results in storage devices (recording devices and reading devices thereof, or the like) connected via these networks.

The present invention is not limited to the first to fifth embodiments and the modified examples thereof, and various inventions may be formed by combining as appropriate a plurality of structural elements disclosed in the respective embodiments and modified examples. For example, formation by excluding some of the structural elements from the whole structural elements illustrated in the respective embodiments and modified examples may be made, or formation by combining as appropriate the structural elements illustrated in the different embodiments and modified examples may be made.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus, comprising:
  a processor comprising hardware, wherein the processor is configured to:
    estimate imaging distances to a subject shown in pixels within an intraluminal image;
    set a plurality of rectangular examination candidate regions in the intraluminal image; and
    set at least one of the plurality of rectangular examination candidate regions as an examination region based on a determination that a distribution of the imaging distances to the subject shown in the pixels within the at least one of the plurality of rectangular examination candidate regions is within a predetermined range;
    identify whether or not a microstructure of the subject shown in the examination region is abnormal, by using texture feature data that enables identification of an abnormality in the microstructure of the subject shown in the examination region, the texture feature data being specified according to the examination region; and
    generate a processed image for display, the processed image showing a result of the identification of the abnormality in the microstructure of the subject shown in the examination region.

2. The image processing apparatus according to claim 1, wherein the processor is configured to:
  acquire a representative imaging distance to the subject shown at a position where the at least one of the plurality of rectangular examination candidate regions is to be set; and
  set the at least one of the plurality of rectangular examination candidate regions of a size according to the representative imaging distance.

3. The image processing apparatus according to claim 1, wherein the processor is configured to:
  calculate a representative imaging distance gradient of the subject shown at a position where the at least one of the plurality of rectangular examination candidate regions is to be set; and
  set the at least one of the plurality of rectangular examination candidate regions of a size according to the representative imaging distance gradient.

4. The image processing apparatus according to claim 1, wherein the processor is configured to:
  calculate a distribution range of the imaging distances to the subject shown in the pixels within the at least one of the plurality of rectangular examination candidate regions; and
  set the at least one of the plurality of rectangular examination candidate regions as the examination region based on a determination that the distribution range is equal to or less than a predetermined threshold value.

5. The image processing apparatus according to claim 1, wherein the processor is configured to:
  calculate a variance of the imaging distances to the subject shown in the pixels within the at least one of the plurality of rectangular examination candidate regions;
  set the at least one of the plurality of rectangular examination candidate regions as the examination region based on a determination that the variance is equal to or less than a predetermined threshold value.

6. The image processing apparatus according to claim 1, wherein the processor is configured to:
  classify values of the imaging distances into one level or a plurality of levels;
  divide the intraluminal image into one region or a plurality of regions, for each region where the subject at a same level of imaging distance is shown; and
  set each of the one region or the plurality of regions acquired as an individual examination region.

7. The image processing apparatus according to claim 1, wherein the processor is configured to:
  calculate, as the texture feature data, a particular spatial frequency component that enables identification of the abnormality in the microstructure of the subject shown in the examination region; and perform statistical classification based on the particular spatial frequency component.

8. The image processing apparatus according to claim 7, wherein the processor is configured to:
select a particular wavelength component specified according to a degree of absorption or scattering in a living body; and
calculate the particular spatial frequency component with respect to the particular wavelength component.

9. The image processing apparatus according to claim 7, wherein the processor is configured to:
calculate a ratio between particular wavelength components having different degrees of absorption or scattering in the living body; and
calculate the particular spatial frequency component with respect to the ratio between the particular wavelength components.

10. The image processing apparatus according to claim 7, wherein the processor is configured to:
acquire a representative imaging distance to the subject shown in the examination region; and
specify a frequency of the particular spatial frequency component according to the representative imaging distance and calculate the particular spatial frequency component.

11. The image processing apparatus according to claim 1, wherein the processor is configured to deform an image in the examination region.

12. The image processing apparatus according to claim 11, wherein the processor is configured to:
acquire a representative imaging distance to the subject shown in the examination region;
normalize a size of the examination region according to the representative imaging distance;
identify whether or not the microstructure of the subject shown in the examination region is abnormal, by using the texture feature data that enables identification of the abnormality in the microstructure of the subject shown in the examination region, the texture feature data being specified according to the examination region having the size that has been normalized.

13. The image processing apparatus according to claim 11, wherein the processor is configured to:
estimate three dimensional coordinates for at least three reference points on the subject shown in the examination region, based on the imaging distances and coordinates of corresponding pixels in the intraluminal image; and
transform on the examination region such that an image of the examination region is acquired by imaging the examination region in a plane passing through the at least three reference points from a front at a given distance.

14. The image processing apparatus according to claim 1, wherein the intraluminal image is formed of a plurality of wavelength components, and wherein the processor is configured to:
select, from the plurality of wavelength components, a low absorbance wavelength component that is a wavelength component with a lowest degree of absorption or scattering in a living body; and
estimate the imaging distances to the subject shown in the pixels within the intraluminal image, based on the low absorbance wavelength component.

15. The image processing apparatus according to claim 1, wherein the processor is configured to:
set at least one of the plurality of rectangular examination candidate regions not set as an examination region as a non-examination target region; and
exclude the non-examination target region included in the intraluminal image.

16. The image processing apparatus according to claim 15, wherein the non-examination target region is any one of a dark region, a bright region, and a region where a residue or bubble is shown, in the intraluminal image.

17. An image processing method comprising:
estimating imaging distances to a subject shown in pixels within an intraluminal image;
setting a plurality of rectangular examination candidate regions in the intraluminal image; and
setting the at least one of the plurality of rectangular examination candidate regions as an examination region based on a determination that a distribution of the imaging distances to the subject shown in the pixels within the at least one of the plurality of rectangular examination candidate regions is within a predetermined range; identifying whether or not a microstructure of the subject shown in the examination region is abnormal, by using texture feature data that enables identification of an abnormality in the microstructure of the subject shown in the examination region, the texture feature data being specified according to the examination region; and
generating a processed image for display, the processed image showing a result of the identification of the abnormality in the microstructure of the subject shown in the examination region.

18. A non-transitory computer-readable recording device with an executable program stored thereon, the program instructing a processor to perform a process comprising:
estimating imaging distances to a subject shown in pixels within an intraluminal image;
setting a plurality of rectangular examination candidate regions in the intraluminal image; and
setting at least one of the plurality of rectangular examination candidate regions as an examination region based on a determination that a distribution of the imaging distances to the subject shown in the pixels within the at least one of the plurality of rectangular examination candidate regions is within a predetermined range; identifying whether or not a microstructure of the subject shown in the examination region is abnormal, by using texture feature data that enables identification of an abnormality in the microstructure of the subject shown in the examination region, the texture feature data being specified according to the examination region; and
generating a processed image for display, the processed image showing a result of the identification of the abnormality in the microstructure of the subject shown in the examination region.

* * * * *